United States Patent
Burns et al.

(10) Patent No.: US 9,732,046 B2
(45) Date of Patent: Aug. 15, 2017

(54) SUBSTITUTED 1,2,4-TRIAZINES AS TUBULIN INHIBITORS

(71) Applicant: YM Biosciences Australia Pty Ltd., Foster City, CA (US)

(72) Inventors: Christopher John Burns, Notting Hill (AU); Andrew Frederick Wilks, South Yarra (AU); Michael Francis Harte, View Bank (AU); Harrison Sikanyika, Kilsyth (AU); Emmanuelle Fantino, Keperra (AU)

(73) Assignee: YM BIOSCIENCES AUSTRALIA PTY LTD., Foster City, CA (US)

( * ) Notice: Subject to any disclaimer, the term of this patent is extended or adjusted under 35 U.S.C. 154(b) by 98 days.

(21) Appl. No.: 14/811,503

(22) Filed: Jul. 28, 2015

(65) Prior Publication Data

US 2016/0031835 A1    Feb. 4, 2016

Related U.S. Application Data

(60) Division of application No. 14/194,543, filed on Feb. 28, 2014, now Pat. No. 9,139,560, which is a continuation of application No. 13/797,568, filed on Mar. 12, 2013, now abandoned, which is a continuation of application No. 13/183,348, filed on Jul. 14, 2011, now Pat. No. 8,394,806, which is a division of application No. 10/581,534, filed as (Continued)

(30) Foreign Application Priority Data

Dec. 3, 2003 (AU) ............................ 2003906680

(51) Int. Cl.
| | | |
|---|---|---|
| A61K 31/53 | (2006.01) | |
| C07D 253/07 | (2006.01) | |
| C07D 213/74 | (2006.01) | |
| C07D 239/42 | (2006.01) | |
| C07D 241/20 | (2006.01) | |
| C07D 401/12 | (2006.01) | |
| C07D 401/14 | (2006.01) | |
| C07D 403/12 | (2006.01) | |

(52) U.S. Cl.
CPC ......... *C07D 253/07* (2013.01); *C07D 213/74* (2013.01); *C07D 239/42* (2013.01); *C07D 241/20* (2013.01); *C07D 401/12* (2013.01); *C07D 401/14* (2013.01); *C07D 403/12* (2013.01)

(58) Field of Classification Search
CPC .......................... A61K 31/53; C07D 253/07
USPC ........................................ 514/242; 544/182
See application file for complete search history.

(56) References Cited

U.S. PATENT DOCUMENTS

| 4,367,790 A | 1/1983 | Draeger |
|---|---|---|
| 4,676,301 A | 6/1987 | Sakamoto |

(Continued)

FOREIGN PATENT DOCUMENTS

| DE | 82928 C | 10/1895 |
|---|---|---|
| DE | 19853278 A1 | 5/2000 |

(Continued)

OTHER PUBLICATIONS

Jordan, V. C. Nature Reviews: Drug Discovery, 2, 2003, 205.*

(Continued)

*Primary Examiner* — Douglas M Willis

(57) ABSTRACT

Compounds of general formula (I), (II), (III) and (V) are described for use in modulating microtubule polymerization and in the treatment of associated disease states. Use of compounds (I), (III) and (V) in the treatment of kinase-associated disease states is also described. Further described are novel compounds of formula (II), (III) and (V).

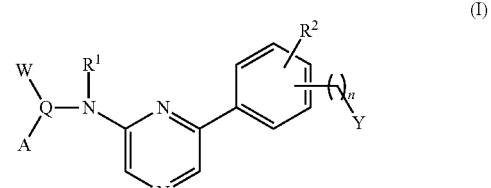

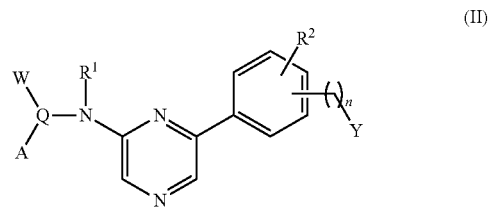

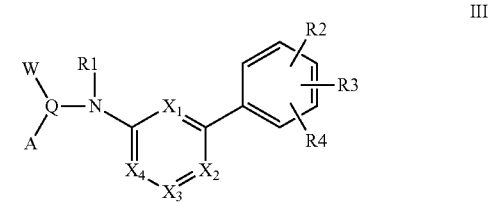

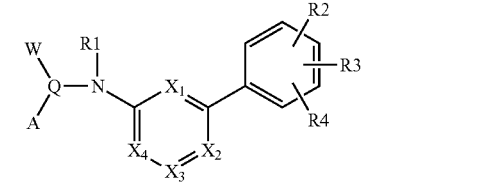

4 Claims, No Drawings

Related U.S. Application Data application No. PCT/AU2004/001689 on Dec. 3, 2004, now Pat. No. 7,981,900.

(56) References Cited

U.S. PATENT DOCUMENTS

| | | | |
|---|---|---|---|
| 7,122,550 | B2 | 10/2006 | Burns et al. |
| 7,981,900 | B2 | 7/2011 | Burns et al. |
| 8,084,456 | B2 | 12/2011 | Burns et al. |
| 8,394,806 | B2 | 3/2013 | Burns et al. |
| 9,139,560 | B2 | 9/2015 | Burns et al. |
| 2004/0235862 | A1 | 11/2004 | Burns et al. |
| 2006/0148824 | A1 | 7/2006 | Burns et al. |
| 2009/0281119 | A1 | 11/2009 | Burns et al. |
| 2013/0274263 | A1 | 10/2013 | Burns et al. |

FOREIGN PATENT DOCUMENTS

| | | |
|---|---|---|
| EP | 0967452 A2 | 12/1999 |
| EP | 0967452 A3 | 12/1999 |
| FR | 352807 A | 8/1905 |
| GB | 253816 A | 6/1926 |
| GB | 1027717 A | 4/1966 |
| GB | 1430729 A | 4/1976 |
| JP | S5088079 A | 7/1975 |
| JP | 2000180093 A | 6/2000 |
| JP | 2005535596 A | 11/2005 |
| JP | 2006514685 A | 5/2006 |
| JP | 4772690 B2 | 9/2011 |
| WO | WO-97/19065 A1 | 5/1997 |
| WO | WO-9827098 A1 | 6/1998 |
| WO | WO-0117995 A1 | 3/2001 |
| WO | WO-0211724 A2 | 2/2002 |
| WO | WO-0211724 A3 | 2/2002 |
| WO | WO-0220495 A2 | 3/2002 |
| WO | WO-0220495 A3 | 3/2002 |
| WO | WO-0222605 A1 | 3/2002 |
| WO | WO-0246170 A2 | 6/2002 |
| WO | WO-0246170 A8 | 6/2002 |
| WO | WO-0247690 A1 | 6/2002 |
| WO | WO-02/060492 A1 | 8/2002 |
| WO | WO-02/079197 | 10/2002 |
| WO | WO-03026661 A1 | 4/2003 |
| WO | WO-03031406 A2 | 4/2003 |
| WO | WO-03031406 A3 | 4/2003 |
| WO | WO-03/099796 A1 | 12/2003 |
| WO | WO-04000318 A2 | 12/2003 |
| WO | WO-04000318 A3 | 12/2003 |
| WO | WO-2004/041789 A1 | 5/2004 |
| WO | WO-2004/041810 A1 | 5/2004 |
| WO | WO-2004043926 A1 | 5/2004 |
| WO | WO-2004052868 A1 | 6/2004 |
| WO | WO-2004085409 A2 | 10/2004 |
| WO | WO-2004085409 A3 | 10/2004 |
| WO | WO-2004089286 A2 | 10/2004 |
| WO | WO-2004089286 A3 | 10/2004 |
| WO | WO-2005003101 A2 | 1/2005 |
| WO | WO-2005003101 A3 | 1/2005 |
| WO | WO-2005/012262 A1 | 2/2005 |
| WO | WO-2005054199 A1 | 6/2005 |
| WO | WO-2006133498 A1 | 12/2006 |
| WO | WO-2008092199 A1 | 8/2008 |

OTHER PUBLICATIONS

Hackam, et al. JAMA, 296(14), 2006, 1731-1732.*
Taylor, et al. Journal of Organic Chemistry, 54(6), 1989, 1456-1459.*
Abramson, N. (May 1, 2006). "Re: "Just Another Kinase" or Is It Special," Clinical Hematology/Oncology Newsletter, pp. 1-3.
Advisory Action mailed on Jan. 31, 2011 for U.S. Appl. No. 10/581,534, filed Jun. 1, 2006, 2 pages.
Advisory Action mailed on Jan. 5, 2011 for U.S. Appl. No. 10/538,499, filed Aug. 3, 2006, 4 pages.
Advisory Action mailed on Jul. 1, 2010 for U.S. Appl. No. 10/581,534, filed Jun. 1, 2006, 3 pages.
Australian Office Action mailed on May 15, 2008 for Au Patent Application No. 2004294354, filed on Dec. 3, 2004, 2 pages.
Australian Office Action mailed on Nov. 7, 2008 for AU Patent Application No. 2003285211, filed on Dec. 11, 2003, 3 pages.
Berge, S.M. et al. (Jan. 1977). "Pharmaceutical Salts," Journal of Pharmaceutical Sciences 66(1):1-19.
Canadian Notice of Allowance mailed on Jul. 11, 2013 for CA Patent Application No. 2,508,170, filed on Dec. 11, 2003, 1 page.
Canadian Office Action mailed on Apr. 10, 2013 for CA Patent Application No. 2,545,422, filed on Dec. 3, 2004, 5 pages.
Canadian Office Action mailed on Apr. 13, 2011 for CA Patent Application No. 2,545,422, filed on Dec. 3, 2004, 6 pages.
Canadian Office Action mailed on Aug. 29, 2012 for CA Patent Application No. 2,545,422, filed on Dec. 3, 2004, 2 pages.
Canadian Office Action mailed on Dec. 20, 2012 for Canadian Patent Application No. 2,508,170, 2 pages.
Canadian Office Action mailed on Jan. 10, 2012 for CA Patent Application No. 2,545,422, filed on Dec. 3, 2004, 3 pages.
Canadian Office Action mailed on Jan. 15, 2014 for CA Patent Application No. 2,545,422, filed on Dec. 3, 2004, 2 pages.
Canadian Office Action mailed on Jul. 6, 2010 for CA Patent Application No. 2,508,170, filed on Dec. 11, 2003, 3 pages.
Canadian Office Action mailed on Mar. 29, 2011 for CA Patent Application No. 2,508,170, filed on Dec. 11, 2003, 3 pages.
Chawla, et al. Curr. Res. & Info. Pharm. Sci. (CRIPS), 5, 1, 2004, pp. 9-12.
Chinese Office Action mailed on Apr. 15, 2011 for CN Patent Application No. 200380105776.X, filed on Dec. 11, 2003, 8 pages. (with English Translation).
Chinese Office Action mailed on Feb. 18, 2010 for CN Patent Application No. 200380105776.X, filed on Dec. 11, 2003, 6 pages. (with English Translation).
Chinese Office Action mailed on Feb. 28, 2013 for CN Patent Application No. 201010621579.5, filed on Dec. 3, 2004, 5 pages. (with English Translation).
Chinese Office Action mailed on Jan. 17, 2012 for CN Patent Application No. 200380105776.X, filed on Dec. 11, 2003, 16 pages. (with English Translation).
Chinese Office Action mailed on Jan. 18, 2012 for CN Patent Application No. 201010621579.5, filed on Dec. 3, 2004, 6 pages. (with English Translation).
Chinese Office Action mailed on Jun. 28, 2010 for CN Patent Application No. 200480036106.1, filed on Dec. 3, 2004, 12 pages. (with English Translation).
Chinese Office Action mailed on Jun. 5, 2009 for CN Patent Application No. 200480036106.1, filed on Dec. 3, 2004, 10 pages. (with English Translation).
Chinese Office Action mailed on Mar. 9, 2007 for CN Patent Application No. 200380105776.X, filed on Dec. 11, 2003, 8 pages. (with English Translation).
Chinese Office Action mailed on May 30, 2008 for CN Patent Application No. 200480036106.1, filed on Dec. 3, 2004, 17 pages. (with English Translation).
Chinese Office Action mailed on Oct. 16, 2009 for CN Patent Application No. 200380105776.X, filed on Dec. 11, 2003, 6 pages. (with English Translation).
Chinese Office Action mailed on Sep. 11, 2012 for CN Patent Application No. 201010621579.5, filed on Dec. 3, 2004, 6 pages. (with English Translation).
Ding, S. et al. (2002, e-pub. Feb. 2, 2002). "A Combinatorial Scaffold Approach Toward Kinase-Directed Heterocycle Libraries," J. Am. Chem. Soc. 124(8):1594-1596.
Dorwald, F.Z. (2005). "Side Reactions in Organic Synthesis: A Guide to Successful Synthesis Design," Wiley-VCH, Verlag GmbH & Co., KGaA, Weinheim, Preface, pp. IX-X.
Duhe, R.Y. et al. (2001). "Negative Regulation of Janus Kinases," Cell Biochemistry and Biophysics 34(1):17-59.
European Communication mailed on Apr. 7, 2010 for EP Patent Application No. 04801111.8, filed on Dec. 3, 2004, 5 pages.
European Communication mailed on Aug. 25, 2008 for EP Patent Application No. 04801111.8, filed on Dec. 3, 2004, 6 pages.

(56) References Cited

OTHER PUBLICATIONS

European Communication mailed on Aug. 29, 2012 for EP Patent Application No. 10010746.5, filed on Dec. 3, 2004, 7 pages.
European Communication mailed on Dec. 19, 2007 for EP Patent Application No. 03778161.4, filed on Dec. 11, 2003, 6 pages.
European Communication mailed on Jul. 22, 2013 for EP Patent Application No. 10010746.5, filed on Dec. 3, 2004, 10 pages.
European Communication mailed on Jun. 15, 2009 for EP Patent Application No. 04801111.8, filed on Dec. 3, 2004, 7 pages.
European Communication mailed on Oct. 11, 2006 for EP Patent Application No. 03727001.4, filed on May 23, 2003, 3 pages.
European Communication mailed on Sep. 15, 2009 for EP Patent Application No. 04801111.8, filed on Dec. 3, 2004, 7 pages.
European Communication regarding Intent to Grant mailed on Aug. 18, 2010 for EP Patent Application No. 04801111.8, filed on Dec. 3, 2004, 5 pages.
European Communication regarding Intent to Grant mailed on Jan. 21, 2013 for EP Patent Application No. 06741240.3, filed on Jun. 15, 2006, 6 pages.
European Communication regarding Intent to Grant mailed on May 3, 2007, for EP Patent Application No. 03727001.4, filed on May 23, 2003, 4 pages.
European Search Report mailed on Dec. 6, 2010 for EP Patent Application No. 10010746.5, filed on Dec. 3, 2004, 14 pages.
European Supplementary Search Report mailed on Jul. 17, 2007 for EP Patent Application No. 03778161.4, filed on Dec. 11, 2003, 3 pages.
European Supplementary Search Report mailed on Mar. 22, 2006 for EP Patent Application No. 03727001.4, filed on May 23, 2003, 3 pages.
European Supplementary Search Report mailed on Oct. 28, 2010 for EP Patent Application No. 06741240.3, filed on Jun. 15, 2006, 5 pages.
Final Office Action mailed on Aug. 6, 2012 for U.S. Appl. No. 13/183,348, filed Jul. 14, 2011, 10 pages.
Final Office Action mailed on Dec. 20, 2010 for U.S. Appl. No. 10/581,534, filed Jun. 1, 2006, 9 pages.
Final Office Action mailed on Dec. 9, 2011 for U.S. Appl. No. 11/917,752, filed Jul. 14, 2008, 18 pages.
Final Office Action mailed on Mar. 22, 2010 for U.S. Appl. No. 10/538,499, filed Aug. 3, 2006, 9 pages.
Final Office Action mailed on May 25, 2010 for U.S. Appl. No. 10/581,534, filed Jun. 1, 2006, 9 pages.
Final Office Action mailed on Oct. 15, 2009 for U.S. Appl. No. 11/367,248, filed Mar. 2, 2006, 6 pages.
Final Office Action mailed on Oct. 22, 2010 for U.S. Appl. No. 10/538,499, filed Aug. 3, 2006, 8 pages.
Hackam, D.G. et al. (2006). "Translation of Research Evidence From Animals to Humans," *JAMA* 296(14):1731-1732.
India Hearing Notice mailed on Jan. 6, 2014 for Indian Patent Application No. 847/KOLNP/2006, 1 page.
Indian Office Action mailed on Jan. 11, 2013 for IN Patent Application No. 2040/KOLNP/2008, filed on Dec. 11, 2003, 1 page.
Indian Office Action mailed on Jul. 9, 2009 for IN Patent Application No. 847/KOLNP/2006, filed on Dec. 3, 2004, 1 page.
Indian Office Action mailed on May 28, 2007 for IN Patent Application No. 972/KOLNP/2005, filed on Dec. 11, 2003, 2 pages.
Indian Office Action mailed on Nov. 14, 2008 for IN Patent Application No. 847/KOLNP/2006, filed on Dec. 3, 2004, 6 pages.
Inquiry from Examiner reported by Foreign Associate on Feb. 16, 2011 for Japanese Patent Application No. 2005-502293, filed on Dec. 11, 2003, 4 pages.
International Search Report for PCT/AU2004/001689 mailed on Feb. 3, 2005, 3 pages.
International Search Report mailed on Jul. 19, 2006 for PCT Patent Application No. PCT/AU2006/000829, filed on Jun. 15, 2006, 2 pages.
International Search Report mailed on Jul. 4, 2003 for PCT Patent Application No. PCT/AU03/00629, filed on May 23, 2003, 2 pages.
International Search Report mailed on Mar. 11, 2004 for PCT Application No. PCT/AU2003/001661, filed on Dec. 11, 2003, 2 pages.
Israel Office Action reported by Foreign Associate on Feb. 22, 2010 for IL Patent Application No. 175576, filed on Dec. 3, 2004, 4 pages.
Israel Office Action reported by Foreign Associate on May 24, 2009 for IL Patent Application No. 168833, filed on Dec. 11, 2003, 4 pages.
Israel Office Action reported by Foreign Associate on May 29, 2011 for IL Patent Application No. 175576, filed on Dec. 3, 2004, 4 pages.
Israel Office Action reported by Foreign Associate on Nov. 28, 2010 for IL Patent Application No. 168833, filed on Dec. 11, 2003, 2 pages.
Japanese Office Action mailed on Feb. 8, 2011 for JP Patent Application No. 2006-541750, filed on Dec. 3, 2004, 4 pages. (with English Translation).
Japanese Office Action mailed on Jan. 8, 2013 for Japanese Patent Application No. 2011-002891, 19 pages.
Japanese Office Action mailed on Jul. 13, 2010 for JP Patent Application No. 2006-541750, filed on Dec. 3, 2004, 13 pages. (Comments and Summary of Foreign Associate only).
Jordan and Wilson, Curr. Opin. Cell Biol. (1998) 10:123-130.
Jordan et al., J. Mol. Biol. (1986) 187:61-73.
Jordan, V. C. Nature Reviews: Drug Discovery, 2, 2003, p. 205.
Korean Office Action mailed on Apr. 25, 2012 for KR Patent Application No. 10-2011-7031131, filed on Dec. 3, 2004, 1 page.
Korean Office Action mailed on Jun. 27, 2011 for KR Patent Application No. 10-2006-7010930, filed on Dec. 3, 2004, 2 pages.
Korean Office Action mailed on Jun. 28, 2012 for KR Patent Application No. 10-2006-7010930, filed on Dec. 3, 2004, 1 page.
Krasnovskaya, L.S. et al. (1972). "Asymmetric Analysis with the Aid of Reactive Dyes," Journal of General Chemistry of the USSR (English Translation) 42(10):2276-2280.
Kumada, M. et al. (1988). "Phosphine-Nickel Complex Catalyzed Cross-Coupling of Grignard Reagents with Aryl and Alkenyl Halides: 1,2-Dibutylbenzene," Organic Syntheses Collective vol. 6, pp. 407-411.
Mexican Office Action mailed on Mar. 9, 2011 for MX Patent Application No. PA/a/2006/006111, filed on Dec. 3, 2004, 4 pages.
Mexican Office Action mailed on May 15, 2012 for MX Patent Application No. MX/a/2011/007662, filed on Dec. 3, 2004, 4 pages.
Miyaura, N. et al. (1995). "Palladium-Catalyzed Cross-Coupling Reactions of Organoboron Compounds," Chem. Rev. 95:2457-2483.
Negishi, E. (Jul. 1, 2002). "A Genealogy of Pd-Catalyzed Cross-Coupling," Journal of Organometallic Chemistry 653:34-40.
New Zealand Office Action mailed on May 23, 2007 for NZ Patent Application No. 540035, filed on Dec. 11, 2003, 2 pages.
New Zealand Office Action mailed on Nov. 4, 2008 for NZ Patent Application No. 546057, filed on Dec. 3, 2004, 2 pages.
New Zealand Office Action mailed on Oct. 17, 2006 for NZ Patent Application No. 540035, filed on Dec. 11, 2003, 2 pages.
Non-final Office Action mailed on Dec. 11, 2009 for U.S. Appl. No. 11/367,248, filed Mar. 2, 2006, 12 pages.
Non-final Office Action mailed on Dec. 15, 2011 for U.S. Appl. No. 13/183,348, filed Jul. 14, 2011, 9 pages.
Non-final Office Action mailed on Feb. 2, 2010 for U.S. Appl. No. 10/581,534, filed Jun. 1, 2006, 15 pages.
Non-final Office Action mailed on Mar. 22, 2011 for U.S. Appl. No. 11/917,752, filed Jul. 14, 2008, 19 pages.
Non-final Office Action mailed on Mar. 23, 2012 for U.S. Appl. No. 13/183,348, filed Jul. 14, 2011, 8 pages.
Non-final Office Action mailed on Mar. 5, 2009 for U.S. Appl. No. 11/367,248, filed Mar. 2, 2006, 14 pages.
Non-final Office Action mailed on May 12, 2009 for U.S. Appl. No. 11/367,248, filed Mar. 2, 2006, 16 pages.
Non-Final Office Action mailed on Nov. 1, 2013 for U.S. Appl. No. 13/797,568, filed Mar. 12, 2013, 8 pages.
Non-final Office Action mailed on Oct. 12, 2010 for U.S. Appl. No. 10/581,534, filed Jun. 1, 2006, 9 pages.

(56) References Cited

OTHER PUBLICATIONS

Non-final Office Action mailed on Oct. 15, 2009 for U.S. Appl. No. 10/538,499, filed Aug. 3, 2006, 21 pages.
Non-final Office Action mailed on Sep. 12, 2008 for U.S. Appl. No. 11/367,248, filed Mar. 2, 2006, 18 pages.
Notice of Allowance mailed on Aug. 25, 2011 for U.S. Appl. No. 10/538,499, filed Aug. 3, 2006, 10 pages.
Notice of Allowance mailed on Feb. 15, 2011 for U.S. Appl. No. 10/538,499, filed Aug. 3, 2006, 14 pages.
Notice of Allowance mailed on Jan. 25, 2006 for U.S. Appl. No. 10/469,303, filed Dec. 4, 2003, 12 pages.
Notice of Allowance mailed on Mar. 15, 2011 for U.S. Appl. No. 10/581,534, filed Jun. 1, 2006, 11 pages.
Notice of Allowance mailed on May 18, 2011 for U.S. Appl. No. 10/581,534, filed Jun. 1, 2006, 8 pages.
Notice of Allowance mailed on Nov. 9, 2012 for U.S. Appl. No. 13/183,348, filed Jul. 14, 2011, 10 pages.
Rai and Wolff, J. Biol. Chem. (1996) 271:14707-14711.
Scapin, G. (Jun. 2002). "Structural Biology in Drug Design: Selective Protein Kinase Inhibitors," Drug Discovery Today 7(11):601-611.
Sedova, V.F. et al. (1981). "Alkylation and Acylation of 2-Aminopyrimidine N-Oxides," Chemistry of Heterocyclic Compounds 17(11):1105-1112, Khimiya Geterotsiklicheskikh Soedinenii 17(11):1515-1522.
Spiotto, M.T. et al. (2000). "STAT3 Mediates IL-6-Induced Growth Inhibition in the Human Prostate Cancer Cell Line LNCaP," The Prostate 42:88-98.
Stille, J.K. (1986). "The Palladium-Catalyzed Cross-Coupling Reactions of Organotin Reagents with Organic Electrophiles," Angew. Chem. Int. Ed. Engl. 25:508-524.
United Kingdom Office Action mailed on May 4, 2006 for GB Patent Application No. 0510486.4, filed on Dec. 11, 2003, 1 page.
United Kingdom Office Action mailed on Oct. 12, 2005 for GB Patent Application No. 0510486.4, filed on Dec. 11, 2003, 3 pages.
Vippagunta, et al. Advanced Drug Delivery Reviews, 48, 2001, p. 18.
Vishwakarma, J.N. et al. (May 1985). "Reactions of Polarized Keten S,N-Acetals with Guanidine: A Facile General Route to Novel 5,6-Substituted 2-Amino-4-N-alkyl/aryl/N-azacycloalkylaminopyrimidines," Indian Journal of Chemistry 24B(5):466-471.
Wendelin, W. et al. (Jan.-Feb. 1984). "Dihydropyrimidines and Related Structures. I. N.sup.2-Substituted 2-Pyrimidinamines and Dihydro-2-pyrimidinamines by Reaction of Phenylbutenones and Monosubstituted Guanidines,"Journal of Heterocyclic Chemistry21(1):65-69.
Wolff, Manfred E., Ed. Burgers Medicinal Chemistry and Drug Discovery—Fifth Edition, New York: John Wiley & Sons, 1996, vol. 1, 975-976.
Written Opinion mailed on Feb. 3, 2005 for PCT Patent Application No. PCT/AU2004/001689, filed on Dec. 3, 2004, seven pages.
Written Opinion mailed on Jul. 19, 2006 for PCT Patent Application No. PCT/AU2006/000829, filed on Jun. 15, 2006, 5 pages.
Zimmermann, J. et al. (1996). "Phenylamino-Pyrimidine (PAP) Derivatives: A New Class of Potent and Selective Inhibitors of Protein Kinase C (PKC)," Archiv der Pharmazie 329(7):371-376.

\* cited by examiner

SUBSTITUTED 1,2,4-TRIAZINES AS TUBULIN INHIBITORS

CROSS-REFERENCE TO RELATED APPLICATIONS

This application is a continuation of U.S. Ser. No. 10/581,534 with an international filing date of 3 Dec. 2004, and now allowed, which claims benefit under 35 U.S.C. §119(e) to International application No. PCT/AU2004/001689 filed 3 Dec. 2004, which claims benefit of Australian Application No. 2003906680 filed 3 Dec. 2003. The contents of these applications are incorporated herein by reference.

The content of the following submission on ASCII text file is incorporated herein by reference, in its entirety: a computer readable form (CRF) of the Sequence Listing (file name: YM010PFUSDC2D_2015-10-14_Sequence_Listing.txt, date recorded: Oct. 14, 2015, size: 2 kb).

FIELD OF THE INVENTION

The present invention relates to methods of suppressing the growth of cancers and other proliferative diseases by the administration of compounds that act by binding to tubulin and to novel heterocyclic compounds suitable for such administration.

BACKGROUND OF THE INVENTION

There are many human and veterinary diseases that stem from processes of uncontrolled or abnormal cellular proliferation. Most important among these diseases is cancer, the generic name given to a broad range of cellular malignancies characterized by unregulated growth and lack of differentiation. Psoriasis is another disease that is characterized by uncontrolled or abnormal cellular proliferation. Psoriasis is a common chronic skin disease characterized by the presence of dry scales and plaques. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. There is, at present, no general therapeutic cure that exists for psoriasis. Whilst milder cases are often treated with topical cortico-steroids, more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved; inflammatory disease states, where endothelial cells, inflammatory cells and glomerular cells are involved; myocardial infarction, where heart muscle cells are involved; glomerular nephritis, where kidney cells are involved; transplant rejection, where endothelial cells are involved; and infectious diseases such as HIV infection and malaria, where certain immune cells and/or other infected cells are involved.

Inhibition of cellular proliferation can be brought about by several mechanisms, including; alkylating agents; topoisomerase inhibitors; nucleotide analogues; antibiotics; hormone antagonists; and nucleic acid damaging agents; inter alia. One pharmacologically important mechanism of inhibiting cellular proliferation is by means of binding tubulin. Tubulin is an asymmetric dimer composed of alpha and beta subunits, that polymerizes to form structural components of the cytoskeleton called microtubules. Microtubules must be highly dynamic in order to carry out many of their functions. At certain stages of the cell cycle, or in particular cell types or organelles, stable microtubules are required, such as for transport within axons or for ciliary and flagellar movement. Micro-tubules assemble during the G2 phase of the cell cycle, and participate in the formation of the mitotic spindle which facilitates the segregation of sister chromatids during the process of cell division. The essential role of microtubules in cell division and the ability of drugs that interact with tubulin to interfere with the cell cycle have made tubulin a successful target for applications that include anti-cancer drugs, fungicides, and herbicides. Typical tubulin ligands such as colchicine, paclitaxel, the Vinca alkaloids such as vinblastine, the epothilones, the halicondrins, benomyl and mebendazole directly inhibit cell division by binding to tubulin which leads to the arrest of the cell cycle at the G2/M boundary of mitosis. This mechanism is the basis of the therapeutic value of compounds of this type, such as treating gout with colchicine, restenosis with paclitaxel, cancer with paclitaxel, vinblastine, epothilones and halichondrins, and fungal infections with benomyl and malaria and helminths with mebendazole.

Interfering with microtubule dynamics or stability can inhibit cell division in several ways. Both stablilizing microtubules or inhibiting their polymerization will prevent the cytoskeleton restructuring that is required at several points in the cell cycle and lead to an arrest of the cell's progression from one stage in the cell cycle to the next. Three main classes of tubulin-binding drugs, namely colchicine analogues, Vinca alkaloids, and the taxanes, have been identified, each of which possesses a specific binding site on the β-tubulin molecule. Paclitaxel (Taxol™) and related taxanes represent a class of drugs that stabilize microtubules, a process that ultimately leads to the "freezing" of the microtubule structures so that they cannot be restructured (Jordan M. A. and Wilson L., 1998). Subsequent arrest at mitosis induces the apoptotic mechanism to cause cell death. A number of colchicine analogues, as well as several other compounds that bind to the same site on β-tubulin as colchicine disrupt tubulin polymerization and disrupt microtubular formation. Vinblastine and several other vinca-related drugs bind to a site that is distinct from the colchicine site. Compounds that bind at the Vinca-site prevent microtubule formation and destabilize microtubules (Jordan et al, 1986; Rai and Wolff (1996). This invention is therefore directed to compounds that potentially modulate microtubule dynamics by binding to tubulin.

Accordingly, the present invention aims to provide compounds which are directly or indirectly toxic to actively dividing cells and are useful in the treatment of cancer, viral and bacterial infections, vascular restenosis, inflammatory diseases, autoimmune diseases, or psoriasis. The present invention is also directed to therapeutic compositions for treating said conditions. Further aspects of the invention are to provide methods for killing actively proliferating cells, such as cancerous, bacterial, or epithelial cells, and treating all types of cancers, infections, inflammatory, and generally proliferative conditions. A further aspect relates to provide methods for treating other medical conditions characterized by the presence of rapidly proliferating cells, such as psoriasis and other skin disorders.

In one embodiment, the method of the invention is used in the treatment of sarcomas, carcinomas and/or leukemias. Exemplary disorders for which the subject method can be used alone or as part of a treatment regimen include:

fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the method of the invention is to be used to treat disorders such as carcinomas forming from tissue of the breast, prostate, kidney, bladder or colon.

In other embodiments, the method of the invention is used to treat hyperplastic or neoplastic disorders arising in adipose tissue, such as adipose cell tumors, e.g., lipomas, fibrolipomas, lipoblastomas, lipomatosis, hibemomas, hemangiomas and/or liposarcomas.

In still other embodiments, infectious and parasitic agents (e.g. bacteria, trypanosomes, fungi, etc.) can also be controlled using the subject compositions and compounds.

SUMMARY OF THE INVENTION

The present inventors have found that a group of compounds based upon a substituted heterocyclic scaffold inhibit the growth and proliferation of cancer cells. The present inventors have further shown that these compounds can bind to tubulin. Such compounds would also be useful in the treatment of other hyperproliferation related disorders.

Accordingly, in a first aspect the present invention provides a method of modulating microtubule polymerisation in a subject, the method comprising administering a therapeutically effective amount of at least one compound of the general formula

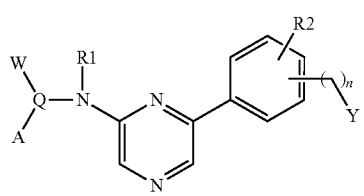

I or pharmaceutically acceptable prodrugs, salts, hydrates, solvates, crystal forms or diastereomers thereof, wherein:
R1 is H, $C_{1-4}$ alkyl;
Q is a bond, or $C_{1-4}$ alkyl;
A is aryl, hetaryl optionally substituted with 0-3 substituents independently chosen from halogen, $C_{1-4}$ alkyl, $CH_2F$, $CHF_2$, $CF_3$, CN, aryl, hetaryl, $OCF_3$, $OC_{1-4}$alkyl, $OC_{2-5}$alkylNR4R5, Oaryl, Ohetaryl, $CO_2R4$, CONR4R5, nitro, NR4R5, $C_{1-4}$ alkylNR4R5, NR6$C_{1-4}$alkylNR4R5, NR4COR5, NR6CONR4R5, NR4$SO_2$R5;
R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR7;
R6 is selected from H, $C_{1-4}$ alkyl;
R7 is selected from H, $C_{1-4}$ alkyl, aryl, hetaryl, $C_{1-4}$ alkyl aryl, $C_{1-4}$ alkyl hetaryl;
R2 is 0-2 substituents independently selected from halogen, $C_{1-4}$alkyl, OH, $OC_{1-4}$alkyl, $CH_2F$, $CHF_2$, $CF_3$, $OCF_3$, CN, $C_{1-4}$alkylNR8R9, $OC_{1-4}$alkylNR8R9, $CO_2R8$, CONR8R9, NR8R9, NR8COR9, NR10CONR8R9, NR8$SO_2$R9;
R8, R9 are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3-8 membered ring optionally containing an atom selected from O, S, NR11;
R10 is selected from H, $C_{1-4}$ alkyl, aryl or hetaryl;
R11 is selected from H, $C_{1-4}$ alkyl, aryl, hetaryl, $C_{1-4}$ alkyl aryl, $C_{1-4}$ alkyl hetaryl;
Y is halogen, OH, NR12R13, NR14COR12, NR14CONR12R13, N14$SO_2$R13;
R12 and R13 are each independently H, $CH_2F$, $CHF_2$, $CF_3$, CN, $C_{1-4}$ alkyl optionally substituted with OH, $OC_{1-4}$alkyl or NR15R16, cycloalkyl; cyclohetalkyl, $C_{1-4}$ alkyl cycloalkyl, $C_{1-4}$ alkyl cyclohetalkyl, or may be joined to form an optionally substituted 3-6 membered ring optionally containing an atom selected from O, S, NR14
R14, R15 and R16 are each independently selected from H, $C_{1-4}$ alkyl;
n=0-4;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16;
R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3-8 membered ring optionally containing an atom selected from O, S, NR17;
R17 is selected from H, $C_{1-4}$ alkyl.

In a second aspect the present invention provides a compound of the general formula

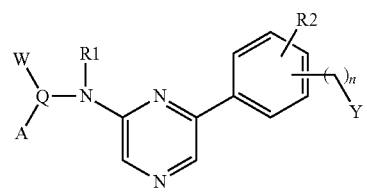

II or pharmaceutically acceptable prodrugs, salts, hydrates, solvates, crystal forms or diastereomers thereof, wherein:
R1 is H, $C_{1-4}$ alkyl;
Q is a bond, or $C_{1-4}$ alkyl;
A is aryl, hetaryl optionally substituted with 0-3 substituents independently chosen from halogen, $C_{1-4}$ alkyl, $CH_2F$, $CHF_2$, $CF_3$, CN, aryl, hetaryl, $OCF_3$, $OC_{1-4}$alkyl, $OC_{2-5}$alkylNR4R5, Oaryl, Ohetaryl, $CO_2R4$, CONR4R5, nitro, NR4R5, $C_{1-4}$ alkylNR4R5, NR6$C_{1-4}$alkylNR4R5, NR4COR5, NR6CONR4R5, NR4$SO_2$R5;

R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR7;

R6 is selected from H, $C_{1-4}$ alkyl;

R7 is selected from H, $C_{1-4}$ alkyl, aryl, hetaryl, $C_{1-4}$ alkyl aryl, $C_{1-4}$ alkyl hetaryl;

R2 is 0-2 substituents independently selected from $C_{1-4}$alkyl and $OC_{1-4}$alkyl;

Y is $CH_2OH$, $OC_{1-4}$alkylOH, $OC_{1-4}$alkylR12, $OC_{1-4}$alkylNR12NR13, C(O)R12, $CH_2R12$, COOR12, CONR12R13, OCONR12R13, $CH_2NR12R13$, NHCOR12, NHCONR12R13, R12 and R13 are each independently H, $C_{1-2}$ alkyl, $(CH_2)_3NEt_2$, $(CH_2)_2NMe_2$, $(CH_2)_5NH_2$, $(CH_2)_2OH$,

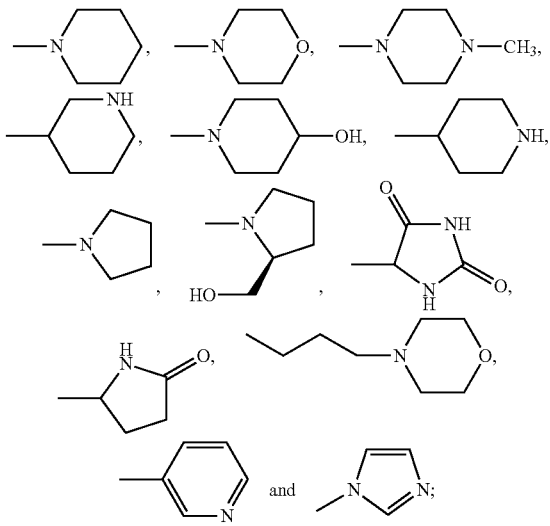

n = 0-4;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16;

R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3-8 membered ring optionally containing an atom selected from O, S, NR17

R17 is selected from H, $C_{1-4}$ alkyl;

wherein when Y is $CH_2R12$ then R12 is not H, $C_{1-2}$alkyl.

In a third aspect, the present invention provides a composition comprising a carrier and at least one compound of the second aspect.

In a fourth aspect the present invention provides a method of treating a hyperproliferation-related disorder in a subject, the method comprising administering a therapeutically effective amount of at least one compound of the second aspect or a composition of the third aspect.

In a fifth aspect the present invention provides a compound of the general formula

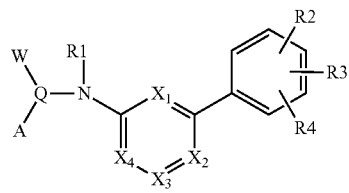

or pharmaceutically acceptable prodrugs, salts, hydrates, solvates, crystal forms or diastereomers thereof, wherein:

$X_1$, $X_2$, $X_3$, $X_4$ are selected from the following:
(i) $X_1$ and $X_2$ are N and $X_3$ and $X_4$ are C independently substituted with Y;
(ii) $X_1$ and $X_4$ are N and $X_2$ and $X_3$ are C independently substituted with Y;
(iii) $X_1$ and $X_3$ are N and $X_2$ and $X_4$ are C independently substituted with Y;
(iv) $X_2$ and $X_4$ are N and $X_1$ and $X_3$ are C independently substituted with Y;
(v) $X_1$ is N and $X_2$, $X_3$, and $X_4$ are C independently substituted with Y;
(vi) $X_3$ is N and $X_1$, $X_2$, and $X_4$ are C independently substituted with Y;
(vii) $X_4$ is N and $X_1$, $X_2$, and $X_3$ are C independently substituted with Y;
(viii) $X_2$ is N and $X_1$, $X_3$, and $X_4$ are C independently substituted with Y; and
(ix) $X_1$, $X_2$ and $X_3$ are N and $X_4$ is C substituted with Y;

R1 is H, $C_{1-6}$alkyl, $C_{1-6}$ alkylNR5R6, $C_{1-6}$alkylNR5COR6, $C_{1-6}$alkylNR5SO$_2$R6, $C_{1-6}$alkylCO$_2$R5, $C_{1-6}$alkylCONR5R6;

R5 and R6 are each independently H, $C_{1-4}$alkyl, aryl, hetaryl, $C_{1-4}$alkylaryl, $C_{1-4}$alkylhetaryl or may be joined to form an optionally substituted 3-8 membered ring optionally containing an atom selected from O, S, NR7;

R7 is selected from H, $C_{1-4}$alkyl;

R2 is selected from $C_{1-6}$alkylOH, $OC_{2-6}$alkylOH, $C_{1-6}$alkylNR8R9, $OC_{2-6}$alkylNR8R9, $C_{1-6}$alkylNR8COR9, $OC_{2-6}$alkylNR8COR9, $C_{1-6}$alkylhetaryl, $OC_{2-6}$alkylhetaryl, OCONR8R9, NR8COOR9, NR10CONR8R9, CONR8R9, NR8COR12;

R8, R9 are each independently H, $C_{1-4}$alkyl, $C_{1-4}$alkylNR11R13, hetaryl, cyclohetalkyl, or may be joined to form an optionally substituted 3-8 membered ring optionally containing an atom selected from O, S, NR14;

R12 is $C_{2-4}$alkyl, $C_{1-4}$alkylNR11R13, hetaryl, cyclohetalkyl;

R11, R13 are each independently H, $C_{1-4}$alkyl, or may be joined to form an optionally substituted 3-8 membered ring optionally containing an atom selected from O, S, NR14;

R14 is selected from H, $C_{1-4}$alkyl;

R10 is H, $C_{1-4}$ alkyl;

R3 and R4 are each independently H, halogen, $C_{1-4}$alkyl, OH, $OC_{1-4}$alkyl, $CF_3$, $OCF_3$;

Q is a bond, or $C_{1-4}$ alkyl;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16;

R15, and R16 are each independently H, $C_{1-4}$alkyl cycloalkyl, $C_{1-4}$alkyl cyclohetalkyl, aryl, hetaryl, or may be joined to form an optionally substituted 3-8 membered ring optionally containing an atom selected from O, S, NR17;
R17 is selected from H, $C_{1-4}$alkyl;

A is aryl, hetaryl optionally substituted with 0-3 substituents independently chosen from halogen, $C_{1-4}$ alkyl, $CF_3$, aryl, hetaryl, $OCF_3$, $OC_{1-4}$alkyl, $OC_{2-5}$alkylNR18R19, Oaryl, Ohetaryl, $CO_2$R18, CONR18R19, NR18R19, $C_{1-4}$ alkylNR18R19, NR2O$C_{1-4}$alkylNR18R19, NR18COR19, NR20CONR18R19, NR18SO$_2$R19;
R18, R19 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR21;
R21 is selected from H, $C_{1-4}$alkyl;
R20 is selected from H, $C_{1-4}$alkyl;

Y is selected from H, $C_{1-4}$alkyl, OH, NR22R23;
R22, R23 are each independently H, $C_{1-4}$alkyl.

In a sixth aspect, the present invention provides a composition comprising a carrier and one or more compounds of the fifth aspect.

In a seventh aspect, the present invention provides a method of treatment of a hyperproliferation-related disorder in a subject, the method comprising administering a therapeutically effective amount of at least one of the compounds of the fifth aspect or a composition according to the sixth aspect.

In an eighth aspect, the present invention consists in a method of treating a protein-kinase related disorder in a subject, the method comprising administering a therapeutically effective amount of at least one of the compounds of the fifth aspect or a composition according to the sixth aspect.

In a ninth aspect, the present invention provides a compound of the general formula

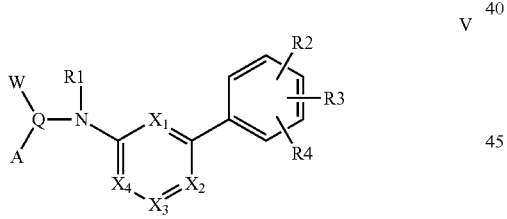

V or pharmaceutically acceptable prodrugs, salts, hydrates, solvates, crystal forms or diastereomers thereof, wherein:
$X_1$, $X_2$, $X_3$, $X_4$ are selected from the following:
(i) $X_1$ and $X_2$ are N and $X_3$ and $X_4$ are C independently substituted with Y;
(ii) $X_1$ and $X_4$ are N and $X_2$ and $X_3$ are C independently substituted with Y;
(iii) $X_2$ and $X_4$ are N and $X_1$ and $X_3$ are C independently substituted with Y;
(iv) $X_1$ is N and $X_2$, $X_3$, and $X_4$ are C independently substituted with Y;
(v) $X_3$ is N and $X_1$, $X_2$, and $X_4$ are C independently substituted with Y;
(vi) $X_4$ is N and $X_1$, $X_2$, and $X_3$ are C independently substituted with Y;
(vii) $X_2$ is N and $X_1$, $X_3$, and $X_4$ are C independently substituted with Y; and
(viii) $X_1$, $X_2$ and $X_3$ are N and $X_4$ is C substituted with Y;

R1 is H, $C_{1-6}$alkyl, $C_{1-6}$ alkylNR5R6, $C_{1-6}$alkylNR5COR6, $C_{1-6}$alkylNR5SO$_2$R6, $C_{1-6}$alkylCO$_2$R5, $C_{1-6}$alkylCONR5R6;
R5 and R6 are each independently H, $C_{1-4}$alkyl, aryl, hetaryl, $C_{1-4}$alkylaryl, $C_{1-4}$alkylhetaryl or may be joined to form an optionally substituted 3-8 membered ring optionally containing an atom selected from O, S, NR7;
R7 is selected from H, $C_{1-4}$ alkyl;
R2 is selected from OH, $OC_{1-6}$alkyl, $C_{1-6}$alkylOH, $OC_{2-6}$alkylOH, $C_{1-6}$alkylNR8R9, $OC_{2-6}$alkylNR8R9, $C_{1-6}$alkylNR8COR9, $OC_{2-6}$alkylNR8COR9, $C_{1-6}$alkylhetaryl, $OC_{2-6}$alkylhetaryl, OCONR8R9, NR8COOR9, NR10CONR8R9, CONR8R9, NR8COR12;
R8, R9 are each independently H, $C_{1-4}$alkyl, $C_{1-4}$alkylNR11R13, hetaryl, cyclohetalkyl, or may be joined to form an optionally substituted 3-8 membered ring optionally containing an atom selected from O, S, NR14;
R12 is $C_{2-4}$alkyl, $C_{1-4}$alkylNR11R13, hetaryl, cyclohetalkyl;
R11, R13 are each independently H, $C_{1-4}$alkyl, or may be joined to form an optionally substituted 3-8 membered ring optionally containing an atom selected from O, S, NR14;
R14 is selected from H, $C_{1-4}$alkyl;
R10 is H, $C_{1-4}$ alkyl;
R3 and R4 are each independently H, halogen, $C_{1-4}$alkyl, OH, $OC_{1-4}$alkyl, $CF_3$, $OCF_3$;
Q is a bond, or $C_{1-4}$alkyl;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16;
R15, and R16 are each independently H, $C_{1-4}$alkyl, $C_{1-4}$alkyl cycloalkyl, $C_{1-4}$alkyl cyclohetalkyl, aryl, hetaryl, or may be joined to form an optionally substituted 3-8 membered ring optionally containing an atom selected from O, S, NR17;
R17 is selected from H, $C_{1-4}$alkyl;
A is aryl, hetaryl optionally substituted with 0-3 substituents independently chosen from halogen, $C_{1-4}$ alkyl, $CF_3$, aryl, hetaryl, $OCF_3$, $OC_{1-4}$alkyl, $OC_{2-5}$alkylNR18R19, Oaryl, Ohetaryl, $CO_2$R18, CONR18R19, NR18R19, $C_{1-4}$ alkylNR18R19, NR2O$C_{1-4}$alkylNR18R19, NR18COR19, NR20CONR18R19, NR18SO$_2$R19;
R18, R19 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR21;
R21 is selected from H, $C_{1-4}$ alkyl;
R20 is selected from H, $C_{1-4}$ alkyl;
Y is selected from H, $C_{1-4}$alkyl, OH, NR22R23;
R22, R23 are each independently H, $C_{1-4}$ alkyl.

In a tenth aspect, the present invention provides a composition comprising a carrier and one or more compounds of the ninth aspect.

In an eleventh aspect, the present invention provides a method of treatment of a hyperproliferation-related disorder in a subject, the method comprising administering a therapeutically effective amount of at least one of the compounds of the ninth aspect or a composition according to the tenth aspect.

In a twelfth aspect, the present invention consists in a method of treating a protein-kinase related disorder in a subject, the method comprising administering a therapeutically effective amount of at least one of the compounds of the ninth aspect or a composition according to the tenth aspect.

DETAILED DESCRIPTION OF THE INVENTION

In a first aspect the present invention provides a method of modulating microtubule polymerisation in a subject, the method comprising administering a therapeutically effective amount of at least one compound of the general formula

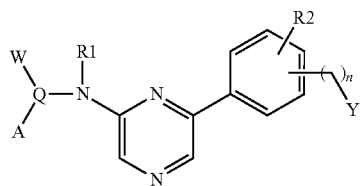

I or pharmaceutically acceptable salts, hydrates, solvates, crystal forms or diastereomers thereof, wherein:
R1 is H, $C_{1-4}$ alkyl;
Q is a bond, or $C_{1-4}$ alkyl;
A is aryl, hetaryl optionally substituted with 0-3 substituents independently chosen from halogen, $C_{1-4}$ alkyl, $CH_2F$, $CHF_2$, $CF_3$, CN, aryl, hetaryl, $OCF_3$, $OC_{1-4}$alkyl, $OC_{2-5}$alkylNR4R5, Oaryl, Ohetaryl, $CO_2R4$, CONR4R5, nitro, NR4R5, $C_{1-4}$ alkylNR4R5, NR6$C_{1-4}$alkylNR4R5, NR4COR5, NR6CONR4R5, NR4SO$_2$R5; and R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR7; and R6 is selected from H, $C_{1-4}$ alkyl; and R7 is selected from H, $C_{1-4}$ alkyl, aryl, hetaryl, $C_{1-4}$ alkyl aryl, $C_{1-4}$ alkyl hetaryl;
R2 is 0-2 substituents independently selected from halogen, $C_{1-4}$alkyl, OH, $OC_{1-4}$alkyl, $CH_2F$, $CHF_2$, $CF_3$, $OCF_3$, CN, $C_{1-4}$alkylNR8R9, $OC_{1-4}$alkylNR8R9, $CO_2R8$, CONR8R9, NR8R9, NR8COR9, NR10CONR8R9, NR8SO$_2$R9; and R8, R9 are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3-8 membered ring optionally containing an atom selected from O, S, NR11; and R10 is selected from H, $C_{1-4}$ alkyl, aryl or hetaryl; and R11 is selected from H, $C_{1-4}$ alkyl, aryl, hetaryl, $C_{1-4}$ alkyl aryl, $C_{1-4}$ alkyl hetaryl;
Y is halogen; OH; NR12R13; NR14COR12; NR14CONR12R13; N14SO$_2$R13; and R12 and R13 are each independently H; $CH_2F$; $CHF_2$; $CF_3$; CN; $C_{1-4}$ alkyl optionally substituted with OH, $OC_{1-4}$alkyl or NR15R16; cycloalkyl; cyclohetalkyl; $C_{1-4}$ alkyl cycloalkyl; $C_{1-4}$ alkyl cyclohetalkyl; or may be joined to form an optionally substituted 3-6 membered ring optionally containing an atom selected from O, S, NR14 and R14, R15 and R16 are each independently selected from H, $C_{1-4}$ alkyl;
n=0-4;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3-8 membered ring optionally containing an atom selected from O, S, NR17 and R17 is selected from H, $C_{1-4}$ alkyl.

Preferably, the method is used in the treatment of a hyperproliferation-related disorder.

Preferably, the compound is selected from the compounds set out in Table 2.

In a second aspect the present invention provides a compound of the general formula

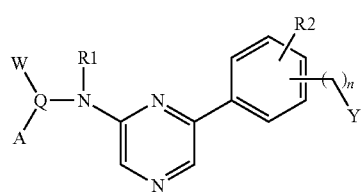

II or pharmaceutically acceptable prodrugs, salts, hydrates, solvates, crystal forms or diastereomers thereof, wherein:
R1 is H, $C_{1-4}$ alkyl;
Q is a bond, or $C_{1-4}$ alkyl;
A is aryl, hetaryl optionally substituted with 0-3 substituents independently chosen from halogen, $C_{1-4}$ alkyl, $CH_2F$, $CHF_2$, $CF_3$, CN, aryl, hetaryl, $OCF_3$, $OC_{1-4}$alkyl, $OC_{2-5}$alkylNR4R5, Oaryl, Ohetaryl, $CO_2R4$, CONR4R5, nitro, NR4R5, $C_{1-4}$ alkylNR4R5, NR6$C_{1-4}$alkylNR4R5, NR4COR5, NR6CONR4R5, NR4SO$_2$R5; and R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR7; and R6 is selected from H, $C_{1-4}$ alkyl; and R7 is selected from H, $C_{1-4}$ alkyl, aryl, hetaryl, $C_{1-4}$ alkyl aryl, $C_{1-4}$ alkyl hetaryl;
R2 is 0-2 substituents independently selected from $C_{1-4}$alkyl and $OC_{1-4}$alkyl;
Y is $CH_2OH$, $OC_{1-4}$alkylR12, $OC_{1-4}$alkylNR12NR13, C(O)R12, $CH_2R12$, COOR12, CONR12R13, OCONR12R13, $CH_2NR12R13$, NHCOR12, NHCONR12R13, and R12 and R13 are each independently H, $C_{1-2}$ alkyl, $(CH_2)_3NEt_2$, $(CH_2)_2NMe_2$, $(CH_2)_5NH_2$, $(CH_2)_2OH$,

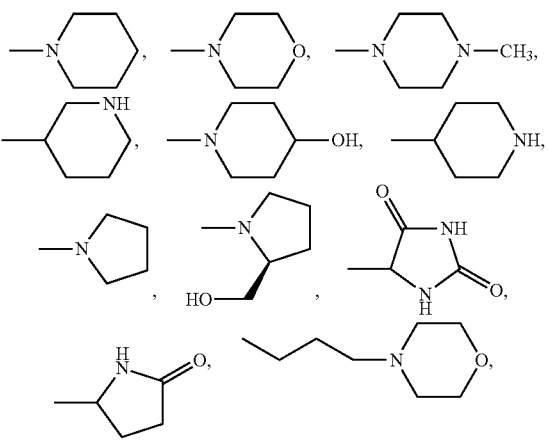

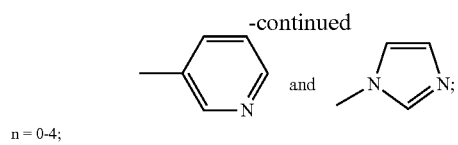

n = 0-4;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3-8 membered ring optionally containing an atom selected from O, S, NR17 and R17 is selected from H, $C_{1-4}$ alkyl;

wherein when Y is CH$_2$R12 then R12 is not H, $C_{1-2}$alkyl.

In a third aspect, the present invention comprises a composition comprising a carrier and at least one compound of the second aspect.

In a fourth aspect the present invention comprises a method of treating a hyperproliferation-related disorder in a subject, the method comprising administering a therapeutically effective amount of at least one compound of the second aspect or a composition of the third aspect.

Preferably, the hyperproliferation-related disorder is treatable by the modulation of microtubule polymerisation.

In a fifth aspect the present invention provides a compound of the general formula

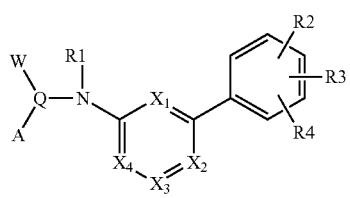

III or pharmaceutically acceptable prodrugs, salts, hydrates, solvates, crystal forms or diastereomers thereof, wherein:

$X_1$, $X_2$, $X_3$, $X_4$ are selected from the following:

(i) $X_1$ and $X_2$ are N and $X_3$ and $X_4$ are C independently substituted with Y;

(ii) $X_1$ and $X_4$ are N and $X_2$ and $X_3$ are C independently substituted with Y;

(iii) $X_1$ and $X_3$ are N and $X_2$ and $X_4$ are C independently substituted with Y;

(iv) $X_2$ and $X_4$ are N and $X_1$ and $X_3$ are C independently substituted with Y;

(v) $X_1$ is N and $X_2$, $X_3$, and $X_4$ are C independently substituted with Y;

(vi) $X_3$ is N and $X_1$, $X_2$, and $X_4$ are C independently substituted with Y;

(vii) $X_4$ is N and $X_1$, $X_2$, and $X_3$ are C independently substituted with Y;

(viii) $X_2$ is N and $X_1$, $X_3$, and $X_4$ are C independently substituted with Y; and (ix) $X_1$, $X_2$ and $X_3$ are N and $X_4$ is C substituted with Y;

R1 is H, $C_{1-6}$ alkylNR5R6, $C_{1-6}$alkylNR5COR6, $C_{1-6}$alkylNR5SO$_2$R6, $C_{1-6}$alkylCO$_2$R5, $C_{1-6}$alkylCONR5R6, where R5 and R6 are each independently H, $C_{1-4}$alkyl, aryl, hetaryl, $C_{1-4}$alkylaryl, $C_{1-4}$alkylhetaryl or may be joined to form an optionally substituted 3-8 membered ring optionally containing an atom selected from O, S, NR7;

R7 is selected from H, $C_{1-4}$alkyl;

R2 is selected from $C_{1-6}$alkylOH, $OC_{2-6}$alkylOH, $C_{1-6}$alkylNR8R9, $OC_{2-6}$alkylNR8R9, $C_{1-6}$alkylNR8COR9, $OC_{2-6}$alkylNR8COR9, $C_{1-6}$alkylhetaryl, $OC_{2-6}$alkylhetaryl, OCONR8R9, NR8COOR9, NR10CONR8R9, CONR8R9, NR8COR12;

R8, R9 are each independently H, $C_{1-4}$alkylNR11R13, hetaryl, cyclohetalkyl, or may be joined to form an optionally substituted 3-8 membered ring optionally containing an atom selected from O, S, NR14;

R12 is $C_{2-4}$alkyl, $C_{1-4}$alkylNR11R13, hetaryl, cyclohetalkyl;

R11, R13 are each independently H, $C_{1-4}$alkyl, or may be joined to form an optionally substituted 3-8 membered ring optionally containing an atom selected from O, S, NR14;

R14 is selected from H, $C_{1-4}$alkyl;

R10 is H, $C_{1-4}$ alkyl;

R3 and R4 are each independently H, halogen, $C_{1-4}$alkyl, OH, $OC_{1-4}$alkyl, CF$_3$, OCF$_3$;

Q is a bond, or $C_{1-4}$ alkyl;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16;

R15, and R16 are each independently H, $C_{1-4}$alkyl, $C_{1-4}$ alkyl cycloalkyl, $C_{1-4}$alkyl cyclohetalkyl, aryl, hetaryl, or may be joined to form an optionally substituted 3-8 membered ring optionally containing an atom selected from O, S, NR17;

R17 is selected from H, $C_{1-4}$alkyl;

A is aryl, hetaryl optionally substituted with 0-3 substituents independently chosen from halogen, $C_{1-4}$ alkyl, CF$_3$, aryl, hetaryl, OCF$_3$, $OC_{1-4}$alkyl, $OC_{2-5}$alkylNR18R19, Oaryl, Ohetaryl, CO$_2$R18, CONR18R19, NR18R19, $C_{1-4}$ alkylNR18R19, NR2OC$_{1-4}$alkylNR18R19, NR18COR19, NR20CONR18R19, NR18SO$_2$R19;

R18, R19 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR21;

R21 is selected from H, $C_{1-4}$alkyl;

R20 is selected from H, $C_{1-4}$alkyl;

Y is selected from H, $C_{1-4}$alkyl, OH, NR22R23;

R22, R23 are each independently H, $C_{1-4}$alkyl.

In the above description it will be appreciated that:

$C_{1-4}$ alkyl means an unsubstituted or optionally substituted straight or branched alkyl chain Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3-8 membered saturated ring

Cyclohetalkyl means an optionally substituted 3-8 membered saturated ring containing 1-3 heteroatoms selected from O, S, NR24, where R24 is H, $C_{1-4}$ alkyl, aryl, hetaryl.

In a preferred embodiment the compound is selected from compounds of the general formula

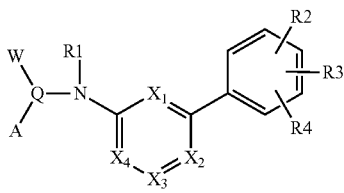

or pharmaceutically acceptable prodrugs, salts, hydrates, solvates, crystal forms or diastereomers thereof, wherein:

$X_1$, $X_2$, $X_3$, $X_4$ are selected from the following:
(i) $X_1$ and $X_2$ are N and $X_3$ and $X_4$ are C independently substituted with Y;
(ii) $X_1$ and $X_4$ are N and $X_2$ and $X_3$ are C independently substituted with Y;
(iii) $X_1$ and $X_3$ are N and $X_2$ and $X_4$ are C independently substituted with Y;
(iv) $X_2$ and $X_4$ are N and $X_1$ and $X_3$ are C independently substituted with Y;
(v) $X_1$ is N and $X_2$, $X_3$, and $X_4$ are C independently substituted with Y;
(vi) $X_3$ is N and $X_1$, $X_2$, and $X_4$ are C independently substituted with Y;
(vii) $X_4$ is N and $X_1$, $X_2$, and $X_3$ are C independently substituted with Y;
(viii) $X_2$ is N and $X_1$, $X_3$, and $X_4$ are C independently substituted with Y; and
(ix) $X_1$, $X_2$ and $X_3$ are N and $X_4$ is C substituted with Y;

R1 is H, $C_{1-6}$alkyl, $C_{1-6}$alkylNR5R6, where R5 and R6 are each independently H, $C_{1-4}$alkyl, aryl, hetaryl, or may be joined to form an optionally substituted 3-8 membered ring optionally containing an atom selected from O, S, NR7;

R7 is selected from H, $C_{1-4}$ alkyl;

R2 is selected from $C_{1-6}$alkylOH, $OC_{2-6}$alkylOH, $C_{1-6}$alkylNR8R9, $OC_{2-6}$alkylNR8R9, $C_{1-6}$alkylNR8COR9, $OC_{2-6}$alkylNR8COR9, $C_{1-6}$alkylhetaryl, $OC_{2-6}$alkylhetaryl, OCONR8R9, NR8COOR9, NR10CONR8R9, CONR8R9, NR8COR12;

R8, R9 are each independently H, $C_{1-4}$alkyl, $C_{1-4}$alkylNR11R13, hetaryl, cyclohetalkyl, or may be joined to form an optionally substituted 3-8 membered ring optionally containing an atom selected from O, S, NR14;

R12 is $C_{2-4}$alkyl, $C_{1-4}$alkylNR11R13, hetaryl, cyclohetalkyl;

R11, R13 are each independently H, $C_{1-4}$alkyl, or may be joined to form an optionally substituted 3-8 membered ring optionally containing an atom selected from O, S, NR14;

R14 is selected from H, $C_{1-4}$alkyl;

R10 is H, $C_{1-4}$alkyl;

R3 and R4 are each independently H, halogen, $C_{1-4}$alkyl, OH, $OC_{1-4}$alkyl, $CF_3$, $OCF_3$;

Q is CH;

W is selected from $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16;

R15, and R16 are each independently H, $C_{1-4}$alkyl, or may be joined to form an optionally substituted 3-8 membered ring optionally containing an atom selected from O, S, NR17;

R17 is selected from H, $C_{1-4}$alkyl;

A is aryl, hetaryl optionally substituted with 0-2 substituents independently chosen from halogen, $C_{1-4}$ alkyl, $CF_3$, aryl, hetaryl, $OCF_3$, $OC_{1-4}$alkyl; $OC_{2-5}$alkylNR18R19, Oaryl, Ohetaryl, $CO_2$R18, CONR18R19, NR18R19, $C_{1-4}$ alkylNR18R19, $NR20C_{1-4}$alkylNR18R19, NR18COR19, NR20CONR18R19, $NR18SO_2R19$;

R18, R19 are each independently H, $C_{1-4}$alkyl, $C_{1-4}$alkyl cyclohetalkyl, aryl, hetaryl, $C_{1-4}$alkyl aryl, $C_{1-4}$alkyl hetaryl, or may be joined to form an optionally substituted 3-8 membered ring optionally containing an atom selected from O, S, NR21;

R21 is selected from H, $C_{1-4}$alkyl;

R20 is selected from H, $C_{1-4}$alkyl;

Y is selected from H, $C_{1-4}$alkyl, NR22R23;

R22, R23 are each independently H, $C_{1-4}$alkyl.

In the above description it will be appreciated that:

$C_{1-4}$ alkyl means an unsubstituted or optionally substituted straight or branched alkyl chain Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3-8 membered saturated ring

Cyclohetalkyl means an optionally substituted 3-8 membered saturated ring containing 1-3 heteroatoms selected from O, S, NR24, where R24 is H, $C_{1-4}$ alkyl, aryl, hetaryl.

In a sixth aspect, the present invention provides a composition comprising a carrier and one or more compounds of the fifth aspect.

In a seventh aspect, the present invention provides a method of treatment of a hyperproliferation-related disorder in a subject, the method comprising administering a therapeutically effective amount of at least one of the compounds of the fifth aspect or a composition according to the sixth aspect.

Preferably, the hyperproliferation-related disorder is treatable by the modulation of microtubule polymerisation.

In an eighth aspect, the present invention consists in a method of treating a protein-kinase related disorder in a subject, the method comprising administering a therapeutically effective amount of at least one of the compounds of the fifth aspect or a composition according to the sixth aspect.

In a ninth aspect, the present invention provides a compound of the general formula

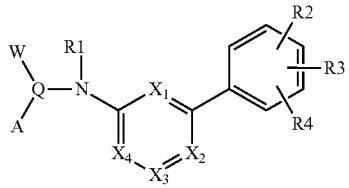

or pharmaceutically acceptable prodrugs, salts, hydrates, solvates, crystal forms or diastereomers thereof, wherein:

$X_1$, $X_2$, $X_3$, $X_4$ are selected from the following:
(i) $X_1$ and $X_2$ are N and $X_3$ and $X_4$ are C independently substituted with Y;
(ii) $X_1$ and $X_4$ are N and $X_2$ and $X_3$ are C independently substituted with Y;

(iii) $X_2$ and $X_4$ are N and $X_1$ and $X_3$ are C independently substituted with Y;
(iv) $X_1$ is N and $X_2$, $X_3$, and $X_4$ are C independently substituted with Y;
(v) $X_3$ is N and $X_1$, $X_2$ and $X_4$ are C independently substituted with Y;
(vi) $X_4$ is N and $X_1$, $X_2$, and $X_3$ are C independently substituted with Y;
(vii) $X_2$ is N and $X_1$, $X_3$, and $X_4$ are C independently substituted with Y; and
(viii) $X_1$, $X_2$ and $X_3$ are N and $X_4$ is C substituted with Y;
R1 is H, $C_{1-6}$alkyl, $C_{1-6}$ alkylNR5R6, $C_{1-6}$alkylNR5COR6, $C_{1-6}$alkylNR5SO$_2$R6, $C_{1-6}$alkylCO$_2$R5, $C_{1-6}$alkylCONR5R6, where R5 and R6 are each independently H, $C_{1-4}$alkyl, aryl, hetaryl, $C_{1-4}$alkylaryl, $C_{1-4}$alkylhetaryl or may be joined to form an optionally substituted 3-8 membered ring optionally containing an atom selected from O, S, NR7;
R7 is selected from H, $C_{1-4}$ alkyl;
R2 is selected from OH, OC$_{1-6}$alkyl, $C_{1-6}$alkylOH, OC$_{2-6}$alkylOH, $C_{1-6}$alkylNR8R9, OC$_{2-6}$alkylNR8R9, $C_{1-6}$alkylNR8COR9, OC$_{2-6}$alkylNR8COR9, $C_{1-6}$alkylhetaryl, OC$_{2-6}$alkylhetaryl, OCONR8R9, NR8COOR9, NR10CONR8R9, CONR8R9, NR8COR12;
R8, R9 are each independently H, $C_{1-4}$alkyl, $C_{1-4}$alkylNR11R13, hetaryl, cyclohetalkyl, or may be joined to form an optionally substituted 3-8 membered ring optionally containing an atom selected from O, S, NR14;
R12 is $C_{2-4}$alkyl, $C_{1-4}$alkylNR11R13, hetaryl, cyclohetalkyl;
R11, R13 are each independently H, $C_{1-4}$alkyl, or may be joined to form an optionally substituted 3-8 membered ring optionally containing an atom selected from O, S, NR14;
R14 is selected from H, $C_{1-4}$alkyl;
R10 is H, $C_{1-4}$ alkyl;
R3 and R4 are each independently H, halogen, $C_{1-4}$alkyl, OH, OC$_{1-4}$alkyl, CF$_3$, OCF$_3$;
Q is a bond, or $C_{1-4}$alkyl;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, OC$_{1-4}$alkyl, NR15R16;
R15, and R16 are each independently H, $C_{1-4}$alkyl, $C_{1-4}$alkyl cycloalkyl, $C_{1-4}$alkyl cyclohetalkyl, aryl, hetaryl, or may be joined to form an optionally substituted 3-8 membered ring optionally containing an atom selected from O, S, NR17;
R17 is selected from H, $C_{1-4}$alkyl;
A is aryl, hetaryl optionally substituted with 0-3 substituents independently chosen from halogen, $C_{1-4}$ alkyl, CF$_3$, aryl, hetaryl, OCF$_3$, OC$_{1-4}$alkyl, OC$_{2-5}$alkylNR18R19, Oaryl, Ohetaryl, CO$_2$R18, CONR18R19, NR18R19, $C_{1-4}$ alkylNR18R19, NR20C$_{1-4}$alkylNR18R19, NR18COR19, NR20CONR18R19, NR18SO$_2$R19;
R18, R19 are each independently H, $C_{1-4}$ alkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR21;
R21 is selected from H, $C_{1-4}$ alkyl;
R20 is selected from H, $C_{1-4}$ alkyl;
Y is selected from H, $C_{1-4}$alkyl, OH, NR22R23;
R22, R23 are each independently H, $C_{1-4}$ alkyl.

In the above description it will be appreciated that:
$C_{1-4}$ alkyl means an unsubstituted or optionally substituted straight or branched alkyl chain
Aryl means unsubstituted or optionally substituted phenyl or naphthyl.
Hetaryl means an unsubstituted or optionally substituted 5- or 6-membered heteroaromatic ring containing one or more heteroatoms selected from O, N, S.
Cycloalkyl means a 3-8 membered saturated ring
Cyclohetalkyl means an optionally substituted 3-8 membered saturated ring containing 1-3 heteroatoms selected from O, S, NR24, where R24 is H, $C_{1-4}$ alkyl, aryl, hetaryl.

In a tenth aspect, the present invention provides a composition comprising a carrier and one or more compounds of the ninth aspect.

In an eleventh aspect, the present invention provides a method of treatment of a hyperproliferation-related disorder in a subject, the method comprising administering a therapeutically effective amount of at least one of the compounds of the ninth aspect or a composition according to the tenth aspect.

Preferably, the hyperproliferation-related disorder is treatable by the modulation of microtubule polymerisation.

In a twelfth aspect, the present invention consists in a method of treating a protein-kinase related disorder in a subject, the method comprising administering a therapeutically effective amount of at least one of the compounds of the ninth aspect or a composition according to the tenth aspect.

The compounds of this invention include all conformational isomers (eg. cis and trans isomers). The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I, II, III, IV and V may also exist as tautomers. This invention relates to the use of all such tautomers and mixtures thereof.

Compounds of formula I, II, III, IV and V having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formulae I, II, III, IV and V. The amino acid residues include the 20 naturally occurring amino acids commonly designated by three letter symbols and also include, 4-hydroxyproline, hydroxylysine, demosine, isodemosine, 3-methylhistidine, norvaline, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formulae I, II, III, IV and V through the carbonyl carbon prodrug sidechain. Prodrugs also include phosphate derivatives of compounds of formulae I, II, III, IV and V (such as acids, salts of acids, or esters) joined through a phosphorus-oxygen bond to a free hydroxyl of compounds of formulae I, II, III, IV and V. Prodrugs also include compounds wherein acyloxyalkyl or phosphonooxyalkyl moieties are covalently attached to compounds of formula I, II, III, IV and V possessing a free hydroxyl group. Acyloxyalkyl or phosphonooxyalkyl moieties may also be covalently attached to compounds of formulae I, II, III, IV and V possessing a pyridyl ring through formation of a N-(acyloxyalkyl)- or N-(phosphonooxyalkyl)-pyridinium salt. This invention also encompasses pharmaceutical compositions containing prodrugs of compounds of the formula I, II, III, IV and V. In addition, this invention encompasses methods of treating or preventing disorders that can be treated or prevented by the modulation of microtubule dynamics comprising administering prodrugs of compounds of the formula I, II, III, IV and V. This invention further encompasses methods of treating or preventing disorders that can be treated or prevented by the disruption of microtubules comprising administering prodrugs of compounds of the formula II, III, IV and V.

In a still further preferred embodiment the compound possesses S chirality at the chiral carbon bearing W, where W is $C_{1-4}$ alkyl or $C_{1-4}$alkylamino. The compound can be used as a purified isomer or as a mixture of any ratio of isomers. It is however preferred that the mixture comprises at least 70%, 80%, 90%, 95%, or 99% of the preferred isomer.

In a yet further preferred embodiment, the present invention provides a compound selected from the compounds of Table 1; compositions comprising a carrier and one or more compounds of Table 1; and, a method of treatment of a hyperproliferation-related disorder in a subject, the method comprising administering at least one of the compounds of Table 1.

More preferably, the hyperproliferation related disorder is treatable by the modulation of microtubule polymerisation.

The present invention further provides for a method of modulating microtubule polymerisation in a subject, the method comprising the administration of a therapeutically effective amount of a compound of any one of Formulas I, II, III, IV and V.

In a preferred embodiment, there is provided a method of modulating microtubule polymerisation in a subject, the method comprising the administration of a therapeutically effective amount of a compound selected from the compounds of Table 1.

The present invention provides that the compounds of formula I, II, III, IV and V may be administered for the treatment of hyperproliferation-related disorders. Preferably, the hyperproliferation-related disorder is treatable by the modulation of microtubule polymerisation. In a preferred embodiment, the hyperproliferation-related disorder or disease state is selected from the group consisting of Cancer, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, and carcinomas forming from tissue of the breast, prostate, kidney, bladder or colon, and neoplastic disorders arising in adipose tissue, such as adipose cell tumors, e.g., lipomas, fibrolipomas, lipoblastomas, lipomatosis, hibemomas, hemangiomas and/or liposarcomas; infectious diseases such as viral, malarial and bacterial infections; vascular restenosis; inflammatory diseases, such as autoimmune diseases, glomerular nephritis myocardial infarction and psoriasis.

The compounds of formula II, II and IV may also be used in the treatment of a hyperproliferation-related disorder or disease state and/or a protein-kinase related disorder or disease state. Preferably, the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV 1, Varicella-Zoster Virus (VZV), Human Papilloma Virus (HPV).

In the treatment or prevention of hyperproliferation-related disorders and/or protein kinase related disorders an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which cell growth inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The terms "administration of" and or "administering a" compound should be understood to mean providing a compound of the invention to the individual in need of treatment.

The present invention provides pharmaceutical compositions comprising at least one of the compounds of the formula I, II, III, IV and V capable of treating a hyperproliferation-related disorder in an amount effective therefore, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I, II, III, IV and V may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following:

Tyrosine kinase inhibitors, such as imatinib (Glivec™), and gefitinib (Iressa™) inter alia; cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen, aspirin, acetaminophen and cyclooxygenase inhibitors such as rofecoxib, steroids such as prednisolone or dexamethasone, gold compounds, antiproliferative agents such as methotrexate, FK506 (tacrolimus, Prograf), mycophenolate mofetil, antineoplastic agents such as azathioprine, VP-16, etoposide, fludarabine, cisplatin, doxorubicin, adriamycin, amsacrine, camptothecin, cytarabine, gemcitabine, fluorodeoxyuridine, melphalan and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

The pharmaceutical composition and method of the present invention may further comprise other therapeutically active compounds as noted herein which are known inhibitors or substrates of drug efflux systems or drug detoxification and excretory systems. Such systems include P-glycoprotein, multidrug resistance-associated protein, lung resistance protein and glutathione S-transferase isoenzymes alpha, mu, pi, sigma, theta, zeta and kappa. Co-administration of drugs known to inhibit or reduce the activity of these systems may increase the efficacy of the compounds described in the present invention through increasing the amount of therapeutic agent in the cell. Using this approach, one may be able to achieve therapeutic efficacy with lower dosages, thus reducing the potential for adverse side effects. Examples of inhibitors or substrates for these systems include; verapamil, probenecid, dipyridamole, ethacrynic acid, indomethacin, sulfasalazine, buthionine sulfoximine, cyclosporin A and tamoxifen.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will now be described by reference to the following non-limiting Examples.

EXAMPLES

Materials and Methods:
Compound Synthesis

Compounds are generally prepared in a 2-step process starting from a dihaloheterocycle.

The first step is a nucleophilic aromatic substitution to generate a monoamino-monohalo intermediate.

The nucleophilic aromatic substitution is typically carried out by addition of a primary or secondary amine to the di-halogenated heterocycle in a solvent such as ethanol, isopropanol, tert-butanol, dioxane, THF, DMF, ethoxyethanol, toluene or xylene. The reaction is typically performed at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalysed amination reaction. Typical catalysts for such transformations include $Pd(OAc)_2/P(t-Bu)_3$, $Pd_2(dba)_3/BINAP$ and $Pd(OAc)_2/BINAP$. These reactions are typically carried out in solvents such as toluene or dioxane, in the presence of bases such as caesium carbonate or sodium or potassium tert-butoxide at temperatures ranging from room temperature to reflux.

The amines employed in the first step of the synthesis of these compounds are obtained commercially or are prepared using methods well known to those skilled in the art. Of particular interest are α-alkylbenzylamines which may be prepared through reduction of oximes. Typical reductants include lithium aluminium hydride, hydrogen gas in the presence of palladium on charcoal catalyst, Zn in the presence of hydrochloric acid, sodium borohydride in the presence of a Lewis acid such as $TiCl_3$, $ZrCl_4$, $NiCl_2$ and $MoO_3$, or sodium borohydride in conjunction with Amberlyst H15 ion exchange resin and LiCl.

α-Alkylbenzylamines may also be prepared by reductive amination of the corresponding ketones. A classical method for such a transformation is the Leuckart-Wallach reaction, though catalytic conditions ($HCO_2NH_4$, $[(CH_3)_5C_5RhCl_2]_2$) or alternative procedures (e.g. $NH_4OAc$, $Na(CN)BH_3$) can also be used.

α-Alkylbenzylamines may also be prepared from the corresponding α-alkylbenzyl alcohols. Such methods include derivatisation of the hydroxyl as a mesylate or tosylate and displacement with a nitrogen nucleophile, such as phthalimide or azide which is converted to the primary amine using conventional synthetic methods; or, displacement of the hydroxyl with a suitable nitrogen nucleophile under Mitsunobu-like conditions. α-Alkylbenzyl alcohols can be prepared by reduction of the corresponding ketones with a reducing agent such as sodium borohydride in a solvent such as methanol. Alternatively, α-alkylbenzyl alcohols can be obtained through addition of an alkyl metal species (such as a Grignard reagent) to a benzaldehyde derivative, typically performed at room temperature or below in solvents such as tetrahydrofuran.

α-Alkyl benzylamines of high optical purity may be prepared from chiral α-alkyl benzyl alcohols using the methods outlined above. The chiral α-alkyl benzyl alcohols may be obtained through chiral reduction of the corresponding ketones. Chiral reducing methods are now well known in organic chemistry and include enzymatic processes, asymmetric hydrogenation procedures and chiral oxazaborolidines.

The second step of the synthesis typically involves a palladium mediated cross-coupling of the monoamino-monochloro intermediate with a suitably functionalised coupling partner. Typical coupling partners are boronic acids or esters (Suzuki coupling: see for example Miyaura, N. and Suzuki, *Chem Rev.* 1995, 952457), stannanes (Stille coupling: see for example Stille, J. K., *Angew. Chem., Int. Ed. Engl.*, 1986, 25, 508), Grignard reagents (Kumada coupling: Kumada, M.; Tamao, K.; Sumitani, K. *Org. Synth.* 1988, Coll. Vol. 6, 407.) or organozinc species (Negishi coupling: Negishi, E.; *J. Organomet. Chem.* 2002, 653, 34).

The Suzuki coupling is the preferred coupling method and is typically performed in a solvent such as DME, THF, DMF, ethanol, propanol, toluene, or 1,4-dioxane in the presence of a base such as potassium carbonate, lithium hydroxide, caesium carbonate, sodium hydroxide, potassium fluoride or potassium phosphate. The reaction may be carried out at elevated temperatures and the palladium catalyst employed may be selected from $Pd(PPh_3)_4$, $Pd(OAc)_2$, $[PdCl_2(dppf)]$, $Pd_2(dba)_3/P(t-Bu)_3$.

The products formed from this reaction sequence may be further derivatised using techniques well-known to those skilled in the art. Alternatively, derivatisation of the mono-amino mono-halo intermediate may be undertaken prior to displacement of the halo substituent. This derivatisation typically involves functionality originally present on the amine species and employs methods well known to those skilled in the art.

Alternatively the preparation sequence can be reversed beginning with the palladium mediated cross-coupling reaction to furnish a mono-halo heterocyclic species. Amine displacement of the halo substituent can then be undertaken using procedures outlined above.

In order that the nature of the present invention may be more clearly understood, preferred forms thereof will now be described with reference to the following non-limiting examples.

Example 1

1-[4-(Trifluoromethyl)phenyl]butan-1-ol

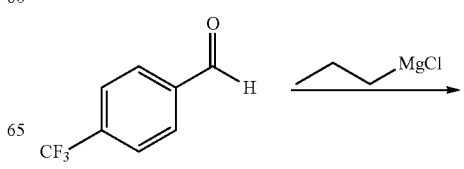

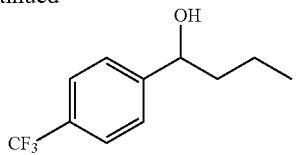

A 2M solution of propylmagnesium chloride in ether (4 ml, 8 mmol) was added to a solution of the aldehyde (1.14 g, 6.6 mmol) in dry THF (10 ml) cooled to 0° C. under $N_2$. The mixture was stirred for 16 h at room temperature, after which time saturated ammonium chloride solution was added. The product was extracted into ethyl acetate, and the ethyl acetate layer dried and concentrated to furnish pure product (1.4 g, 98%).

1H-n.m.r. ($CDCl_3$) δ 0.94 (t, 3H, J=7.2 Hz, $CH_3$), 1.41 (m, 2H, $CH_2$), 1.75 (m, $CH_2$, 2H), 4.77 (br s, 1H, CH), 7.44-7.62 (m, 4H, ArH)

Example 2

1-(1-Azidobutyl)-4-(trifluoromethyl)benzene

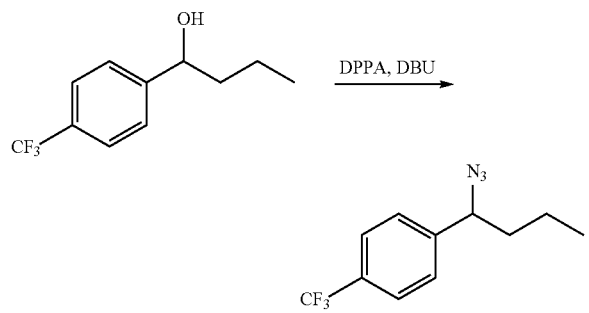

A solution of 1-[4-(trifluoromethyl)phenyl]butan-1-ol (1.4 g, 6.4 mmol) and diphenylphosphoryl azide (2.8 ml, 12.8 mmol) in THF (6 mL) cooled to −10° C. under $N_2$ was treated with DBU (1.9 mL, 12.8 mmol). The resulting solution was stirred at room temperature for 20 hours and then diluted with a mixture of ether and $H_2O$. The organic phase was dried and concentrated and the residue purified by column chromatography using hexane:ethyl acetate (10:1) as eluent to furnish pure azide (0.85 g, 54%).

$^1$H-n.m.r. ($CDCl_3$) δ 0.94 (t, 3H, J=7.2 Hz, $CH_3$), 1.37 (m, 2H, $CH_2$), 1.75 (m, 2H, $CH_2$), 4.50 (t, 1H, CH), 7.42 (d, J=7.8 Hz, 2H, ArH), 7.64 (d, 2H, J=7.8 Hz, ArH)

Example 3

1-[4-(Trifluoromethyl)phenyl]butan-1-amine

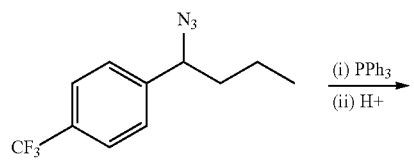

A mixture of 1-(1-azidobutyl)-4-(trifluoromethyl)benzene (0.84 g, 3.5 mmol) and triphenylphosphine (1.8 g, 6.9 mmol) in ethyl acetate (6 mL) and 10% HCl (6 ml) was stirred at room temperature for 64 h. The aqueous phase was collected and the organic phase extracted with 10% HCl (3×5 mL). The aqueous layers were combined and basified with 5M NaOH, and then extracted with ethyl acetate (5×15 mL). The organic phase was dried and concentrated to give pure amine (0.4 g, 54%).

$^1$H-n.m.r. ($CDCl_3$) δ 0.91 (t, J=7.4 Hz, 3H $CH_3$), 1.31 (m, 2H, $CH_2$), 1.62 (m, 2H, $CH_2$), 3.97 (m, 1H, CH), 7.43 (AA'XX', 2H, ArH), 7.58 (AA'XX', 2H, ArH)

Example 4

3-Fluoro-N-methoxy-N-methylbenzamide

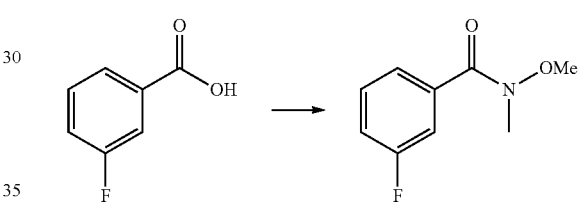

To a suspension of 3-fluorobenzoic acid (140 mg, 1 mmol) and N,O-dimethylhydroxylamine hydrochloride (107 mg, 1.1 mmol) in dichloromethane (2.5 mL) was added 1-[3-(dimethylamino)propyl]-3-ethylcarbodiimide hydrochloride (EDC) (211 mg, 1.1 mmol) and the mixture stirred at room temperature for 75 h. The solvents were removed under reduced pressure and the residue chromatographed using ethyl acetate-hexane (4:6) to separate the pure product (130 mg, 71%).

$^1$H-n.m.r. ($CDCl_3$) δ 3.36 (s, 3H, N-Me), 3.55 (s, 3H, N—OMe), 7.1-7.2 (m, 1H, ArH), 7.3-7.5 (m, 3H, Ar)

Example 5

1-(3-Fluorophenyl)butan-1-one

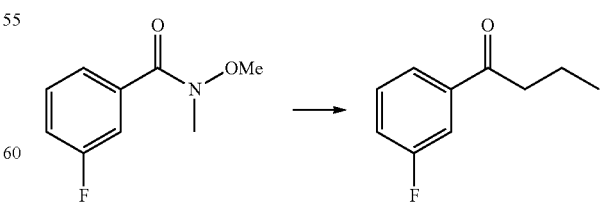

To a solution of 3-fluoro-N-methoxy-N-methylbenzamide (130 mg, 0.71 mmol) in dry THF (2 mL) cooled to −10° C. was added propyl magnesium chloride (532 µl, 2M solution in ether, 1.1 mmol) under nitrogen. The solution was stirred at −10° C. for 1 h and at room temperature for 75 min. The solution was the poured into saturated aqueous ammonium chloride and the product extracted into ethyl acetate (3×25 mL). The organic layers were combined, washed with brine, dried (MgSO$_4$) and concentrated to give a pale yellow oil, which was purified by chromatography using ethyl acetate-hexane (1:9) to separate the pure product (78 mg, 66%).

$^1$H-n.m.r. (CDCl$_3$) δ 1.01 (t, 3H, J=7.4 Hz, Me), 1.77 (m, 2H, CH$_2$CH$_3$), 2.93 (t, J=7.2 Hz, 2H, COCH$_2$), 7.15-7.30 (m, 1H, Ar), 7.35-7.50 (m, 1H, Ar), 7.60-7.70 (m, 1H, Ar), 7.70-7.80 (m, 1H, Ar).

Example 6

1-(5-Methylpyridin-3-yl)butan-1-amine

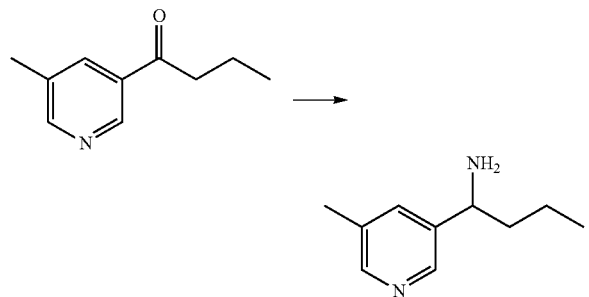

To a solution of 1-(5-methylpyridin-3-yl)butan-1-one (800 mg, 4.9 mmol) and ammonium formate (1.55 g, 24.5 mmol) in methanol (5 mL) under nitrogen was added dichloro(pentamethylcyclopentadienyl)rhodium (LH) dimer (45 mg, 0.074 mmol). The solution was heated at reflux for 8 h. after which time the solution was cooled to room temperature and acidified to pH ~2 with 2M HCl. The mixture was washed with dichloromethane (3×15 mL) and the aqueous phase then basified to pH ~12 by addition of solid KOH. The aqueous phase was extracted with dichloromethane (3×15 mL) and the combined organic layers washed with brine, dried (Na$_2$SO$_4$) and concentrated to give a pure product (620 mg, 77%).

$^1$H-n.m.r. (CDCl$_3$) δ 0.91 (t, 3H, J=7.4 Hz, CH$_2$CH$_2$CH$_3$), 1.14-1.82 (m, 6H, 2×CH$_2$, NH), 2.33 (s, 3H, CH$_3$), 3.91 (t, 1H, J=6.8 Hz, CHNH$_2$), 7.47 (s, 1H, ArH), 8.32 (br s, 2H, Ar).

Example 7

(1R)-1-(4-Fluorophenyl)butan-1-ol

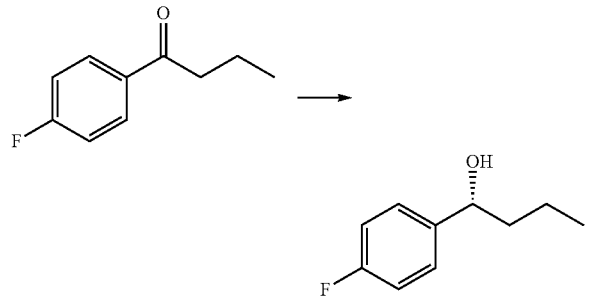

Diethylaniline-borane complex (2.4 mL, 13.4 mmol) was added dropwise over 5 min. to a solution of (1S,2R)-1-aminoindan-2-ol (201 mg, 1.4 mmol) in dry THF (20 mL) cooled to 0° C. under nitrogen. After 40 min. a solution of the ketone in THF (40 mL) was added dropwise over 90 min. The cooling bath was then removed and the solution then stirred at RT for 5 h. Acetone (6 mL) was added and the resulting solution stirred at RT for 60 min. before the solvents were removed under reduced pressure. The residue was dissolved in toluene (100 mL) and washed successively with 1M H$_2$SO$_4$ (4×50 mL), H$_2$O (2×50 mL) and brine (50 mL) and then dried (Na$_2$SO$_4$).

$^1$H-n.m.r. (CDCl$_3$) δ 0.93 (t, 3H, J=7.2 Hz, CH$_2$CH$_2$CH$_3$), 1.17-1.51 (m, 2H, CH$_2$CH$_2$CH$_3$), 1.58-1.82 (m, 2H, CH$_2$CH$_2$CH$_3$), 4.66 (t, J=6.6 Hz, CHNH$_2$), 6.98-7.07 (m, 2H, ArH), 7.26-7.34 (m, 2H, ArH).

Example 8

(1R)-1-Pyridin-3-ylbutan-1-ol

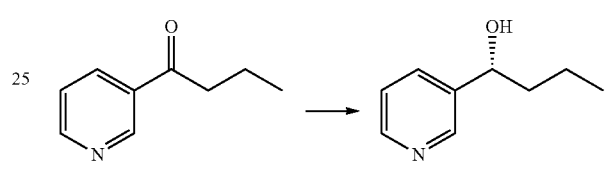

To a solution of S-(−)-α, α-diphenyl-2-pyrrolidinemethanol (500 mg, 2 mmol) and trimethylborate (0.27 ml, 2.4 mmol) in THF (20 mL) was added borane-dimethylsulfide complex (20 mL, 2M in THF, 40 mmol). The mixture was cooled to 0° C. and 1-pyridin-3-ylbutan-1-one was added dropwise over 4 h. The solution was stirred at RT overnight and then treated with 2M HCl (175 mL) and stirring continued for 4 h. The volatiles were removed under reduced pressure and the resulting cloudy solution basified to pH 11 with aqueous ammonia. The product was extracted into ethyl acetate (3×100 mL) and the combined organic layers washed with brine (100 mL) and dried (Na2SO4). Removal of the solvent under reduced pressure afforded ~3 g of product.

$^1$H-n.m.r. (CDCl$_3$) δ 0.94 (t, 3H, J=7.4 Hz, CH$_2$CH$_2$CH$_3$), 1.20-1.54 (m, 2H, CH$_2$CH$_2$CH$_3$), 1.60-1.91 (m, 2H, CH$_2$CH$_2$CH$_3$), 2.64 (br s, 1H, OH), 4.73 (t, 1H, J=6.6 Hz, CHOH), 7.24-7.30 (m, 1H, Ar), 7.68-7.74 (m, 1H, Ar), 8.47-8.52 (m, 2H, Ar).

Example 9

3-Amino-3-phenylpropan-1-ol

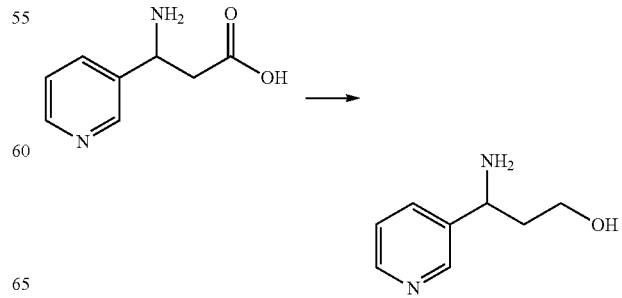

To a suspension of 3-amino-3-phenylpropanoic acid (2.0 g, 12.1 mmol) in dry THF (45 mL) cooled to 0° C. under $N_2$ was added portionwise over 20 minutes solid $LiAlH_4$ (920 mg, 24.2 mmol). Stirring was continued at room temperature for 24 h. after which time solid $Na_2SO_4 \cdot 10H_2O$ was added with stirring until only a heavy white precipitate was present. The organic layer was diluted with ether and filtered through Celite® and the concentrated in vacuo. The residue was dissolved in ethyl acetate (50 mL) and extracted with 1N HCl (3×40 mL). The aqueous layers were combined and basified to pH~12 with 5M NaOH. The aqueous phase was extracted with ethyl acetate (3×50 mL) and the combined organic phases dried ($Na_2SO_4$) and concentrated in vacuo to separate the product which was used without further purification (0.9 g, 49%).

$^1$H-n.m.r. ($CDCl_3$) δ 1.84-1.94 (m, 2H, C$\underline{H}_2$CH$_2$OH), 2.68 (br s, 1H, NH$_2$), 3.79 (t, 2H, J=5.8 Hz, CH$_2$C$\underline{H}_2$OH), 4.08-4.15 (m, 1H, C$\underline{H}$NH$_2$), 4.77 (q, 1H, CH), 7.21-7.38 (m, 5H, ArH)

Example 10

6-Chloro-N-[1-(4-methylphenyl)butyl]pyrazin-2-amine

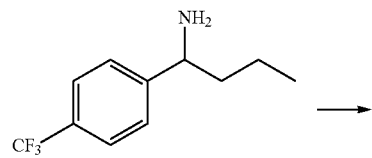

→

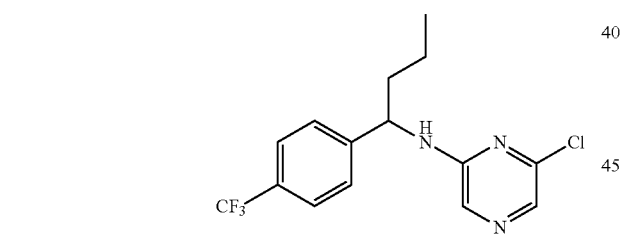

To a solution of 1-[4-(trifluoromethyl)phenyl]butan-1-amine (0.40 g, 1.9 mmol) and 2,6-dichloropyrazine (0.55 g, 3.7 mmol) in 1,4-dioxane (6 mL) was added anhydrous potassium carbonate (0.39 g, 2.8 mmol). The resulting mixture was heated at reflux for 18 h. After cooling to room temperature, the mixture was diluted with ethyl acetate and $H_2O$. The organic phase was collected, dried and concentrated. The residue was purified by flash chromatography eluting with ethyl acetate-hexane (1:1) to give pure product (0.03 g, 5%).

$^1$H-n.m.r. ($CDCl_3$) δ 0.95 (t, 3H, J=7.4 Hz, CH$_3$), 1.39 (m, 2H, CH$_2$), 1.81 (m, 2H, CH$_2$), 4.77 (q, 1H, CH), 5.09 (br d, 1H, NH), 7.42-7.62 (m, 5H, ArH), 7.80 (s, 1H, pyraz.-H)

Example 11

N-(3-(1-[(6-Chloropyrazin-2-yl)amino]butyl)phenyl)acetamide

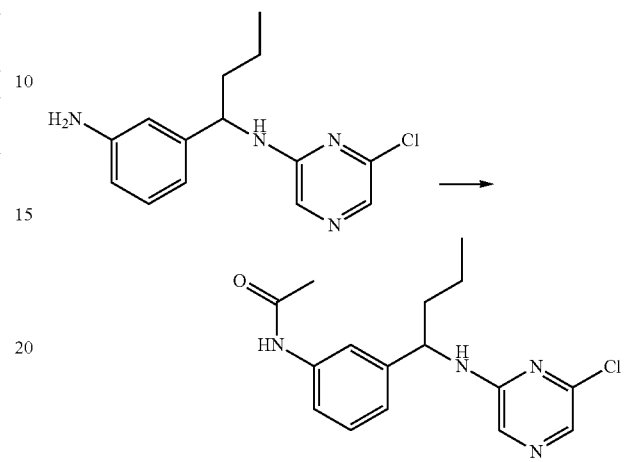

To a stirred solution of N-[1-(3-aminophenyl)butyl]-6-chloropyrazin-2-amine (0.10 g, 0.36 mmol) and triethylamine (100 μl, 0.72 mmol) in dichloromethane (3 mL) cooled to 0° C. was added acetyl chloride (31 μL, 0.43 mmol). The resulting mixture was stirred at room temperature for 18 h. then diluted with dichloromethane (10 mL) and washed with $H_2O$ (10 mL) and brine (10 mL). The organic phase was collected, dried and concentrated and the residue purified by flash chromatography eluting with ethyl acetate-hexane (1:1) to give pure product (94 mg, 82%).

$^1$H-n.m.r. ($CDCl_3$) δ 0.93 (t, 3H, J=7.4 Hz, Me), 1.28-1.43 (m, 2H, CH$_2$), 1.76-1.85 (m, 2H, CH$_2$), 2.16 (s, 3H, COCH$_3$), 4.48-4.59 (m, 1H, C$\underline{H}$CH$_2$CH$_2$CH$_3$), 5.15 (br d, J=6.8 Hz, 1H, NH), 7.06 (d, 1H, J=7.4 Hz, Ar), 7.23-7.33 (m, 3H, Ar), 7.54 (s, 1H, CONH), 7.60 (s, 1H, pyraz-H), 7.77 (s, 1H, pyraz-H).

Example 12

N-[2-Methoxy-4-(6-([(1S)-1-pyridin-3-ylbutyl]amino)pyrazin-2-yl)phenyl]-N'-ethylurea

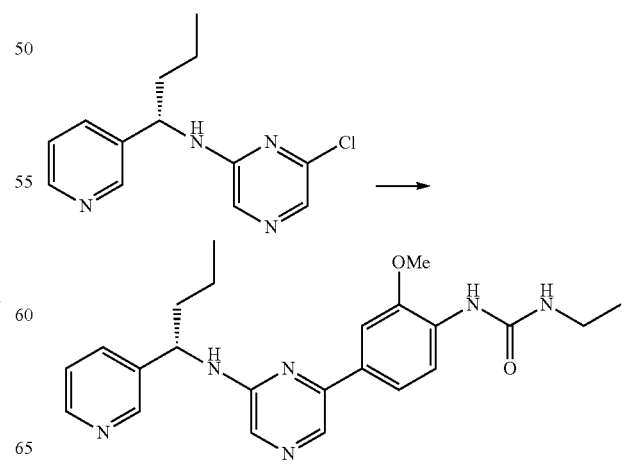

Under a nitrogen atmosphere a mixture of 6-chloro-N-[(1S)-1-pyridin-3-ylbutyl]pyrazin-2-amine (53 g, 0.2 mmol), 4-{[(ethylamino)carbonyl]amino}-3-methoxyphenylboronic acid pinacol diester (69 mg, 0.23 mmol), tetrakis(triphenylphosphine)palladium(0) (23 mg, 0.02 mmol) in toluenen-propanol (2.6 mL, 3:1) was treated with 2M aqueous sodium carbonate solution (0.15 mL, 0.3 mmol). The resulting mixture was stirred vigorously whilst being heated at 100° C. for 22 hours. Once cool ethyl acetate (10 mL) was added and the mixture washed with H$_2$O (6×10 mL) and brine (10 mL) and then dried (Na$_2$SO$_4$). Removal of solvent in vacuo then yielded crude product, which was purified by column chromatography using dichloromethane-methanol-aqueous ammonia (93:7:1) as eluent to furnish the product (60 mg).

$^1$H-n.m.r. (CDCl$_3$) δ 0.98 (t, 3H, J=7.4 Hz, CH$_3$), 1.14 (t, 3H, J=7.2 Hz, CH$_3$), 1.36-1.52 (m, 2H, CH$_2$), 1.78-1.98 (m, 2H, CH$_2$), 2.27 (s, 3H, CH$_3$), 3.23-3.37 (m, 2H, CH$_2$), 4.84-4.94 (m, 2H, CH, NHCONH), 5.19 (d, 1H, J=6.2 Hz, CHNH), 6.31 (s, 1H, ArNH), 7.24-7.30 (m, 1H, ArH), 7.55-7.73 (m, 4H, ArH), 7.75 (s, 1H, pyraz.-H), 8.21 (s, 1H, pyraz.-H), 8.49-8.52 (m, 1H, ArH), 8.69 (d, 1H, J=2.0 Hz, ArH).

Example 13

4-{[(Ethylamino)carbonyl]amino}-3-methylphenylboronic acid pinacol diester

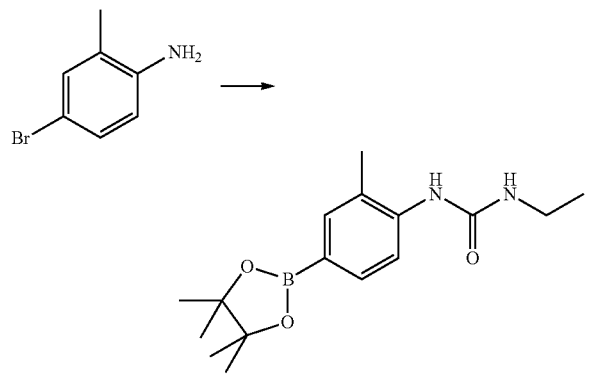

The aniline (500 mg, 2.7 mmol) was dissolved in pyridine (5 mL) and to this was added ethyl isocyanate (424 μL, 5.4 mmol). The resulting solution was stirred overnight during which time a thick precipitate formed which was filtered and dried in vacuo to give the ethyl urea (595 mg, 86%).
$^1$H-n.m.r. (d$_6$-DMSO) δ 1.05 (t, 3H, J=7.4 Hz, CH$_3$), 2.15 (s, 3H, CH$_3$), 3.09 (dq, 2H, J=7.4, 5.4 Hz, CH$_2$), 6.55 (br t, 1H, J=5.4 Hz, NH), 7.24 (dd, 1H, J=8.8, 2.2 Hz, Ar—H), 7.30 (d, 1H, J=2.2 Hz, Ar—H), 7.66 (s, 1H, NH), 7.82 (d, 1H, J=8.8 Hz, ArH).

To a degassed suspension of the ethyl urea bromide (514 mg, 2 mmol), potassium acetate (784 mg, 8 mmol) and bis(pinacolato)diboron (508 mg, 2 mmol) in a mixture of ethanol (10 mL) and dioxane (2 mL) was added dichloro[1,1'-bis(diphenylphosphino)ferrocene]palladium (II) dichloromethane adduct (44 mg, 0.06 mmol). The solution was heated at reflux for 2 h. and then allowed to cool to RT. The solvent was removed under reduced pressure and the residue dissolved in dichloromethane (60 mL). This was washed with H$_2$O (2×30 mL) and brine (30 mL), dried (Na$_2$SO$_4$) and concentrated in vacuo. The residue was chromatographed using ethyl acetate-hexane (1:1) as eluent to separate the pure product as a solid (351 mg, 58%).

$^1$H-n.m.r. (CDCl$_3$) δ 1.12 (t, 3H, J=6.8 Hz, CH$_3$), 1.34 (s, 12H, CH$_3$), 2.26 (s, 3H, CH$_3$), 3.09 (dq, 2H, J=6.8, 5.2 Hz, CH$_2$), 4.69 (br t, 1H, NH), 6.06 (s, 1H, NH), 7.49 (d, 1H, J=7.8 Hz, Ar—H), 7.67 (m, 2H, ArH).

Example 14

5Bromo-N-(1-phenylbutyl)pyridin-3-amine

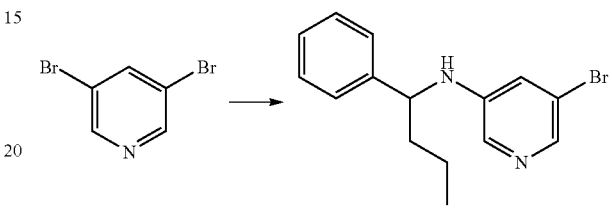

To a degassed solution of 3,5-dibromopyridine (0.4 g, 1.7 mmol), sodium tert-butoxide (227 mg, 3.6 mmol), tris(dibenzylideneacetone)dipalladium (145 mg, 0.09 mmol) and rac-BINAP (105 mg, 0.2 mmol) in dry toluene (10 mL) was added 1-phenylbutan-1-amine (0.2 mL). The mixture was heated at reflux for 24 h and upon cooling to room temperature was diluted with ether and washed with brine (3×30 mL). The solution was dried (Na$_2$SO$_4$) and concentrated and the residue chromatographed using ethyl acetate-hexane (40:60) as eluant. From the early fractions 97 mg of pure product was obtained.

$^1$H-n.m.r. (CDCl$_3$) δ 0.94 (t, 3H, J=7.2 Hz, CH$_3$), 1.21-1.53 (m, 2H, CH$_2$), 1.68-1.87 (m, 2H, CH$_2$), 4.19-4.32 (m, 2H, CH and NH), 6.86 (t, 1H, J=2.0 Hz, ArH), 7.20-7.38 (m, 5H, ArH), 7.88 (d, 1H, J=2.0 Hz, ArH), 7.92 (d, 1H, J=2.0 Hz, ArH).

Example 15

5-[4-(Benzyloxy)-3-methoxyphenyl]-3-chloro-6-methyl-1,2,4-triazine

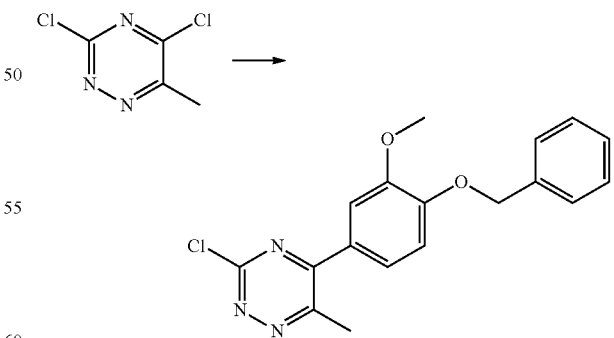

A degassed solution of 3,5-dichloro-6-methyl-1,2,4-triazine (151 mg, 0.9 mmol), 4-(benzyloxy)-3-methoxybenzene boronic acid (236 g, 0.9 mmol), tetrakis(triphenylphosphine) palladium(0) (55 mg, 0.05 mmol) and tripotassium phosphate (249 mg, 1.2 mmol) in dimethoxyethane (5 mL) was heated at reflux for 24 h. Upon cooling to room temperature the solution was diluted with CHCl₃ and filtered through Celite®. The filtrate was concentrated in vacuo and the product purified by column chromatography using ethyl acetate-hexane (25:75) as eluent to furnish (75 mg, 22%).

¹H-n.m.r. (CDCl₃) δ 0.88 (s, 3H, Ar—CH₃), 3.98 (s, 3H, OCH₃), 5.26 (s, 2H, CH₂), 6.99 (d, 1H, J=8.5 Hz, ArH), 7.25-7.44 (m, 7H, ArH).

Example 16

5-[4-(Benzyloxy)-3-methoxyphenyl]-6-methyl-N-(1-phenylpropyl)-1,2,4-triazin-3-amine

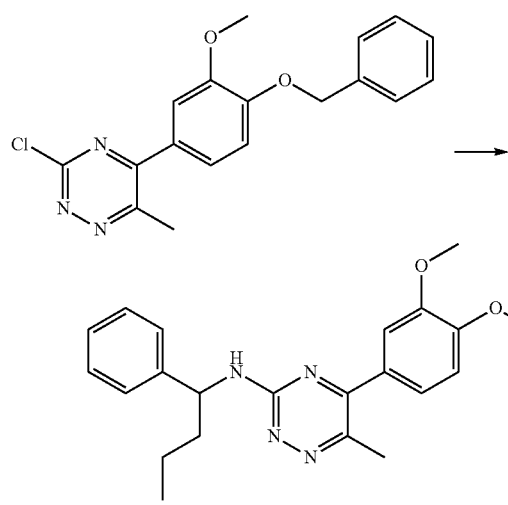

A solution of the triazene (50 mg, 0.14 mmol) in ethoxy-ethanol (2.5 mL) was treated with diisopropylamine (50 μL, 0.28 mmol) and 1-phenylbutan-1-amine (46 μL, 0.28 mmol) and the resulting solution heated at 110° C. for 3 days. The solvent was then removed in vacuo to give an orange residue which was chromatographed using ethyl acetate-dichloromethane (20:80) as eluent to separate the product as a pale yellow solid (60 mg, 90%).

¹H-n.m.r. (CDCl₃) δ 0.94 (t, 3H, CH₃), 1.21-1.53 (m, 2H, CH₂), 1.78-1.97 (m, 2H, CH₂), ☐.62 (s, 3H, Ar—CH₃), 3.89 (s, 3H, OCH₃), 5.10 (br q, 1H, CH₂), 5.22 (s, 2H, CH₂), 5.65 (br s, 1H, NH), 6.87 (d, 1H, J=9.2 Hz, ArH), 7.12-7.44 (m, 12H, Ar—H).

Example 17

2-Chloro-5-methyl-N-[(1S)-1-pyridin-3-ylbutyl]pyrimidin-4-amine

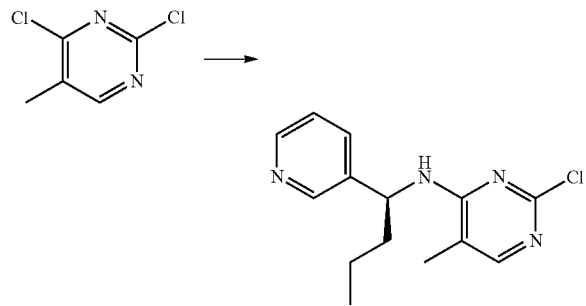

To a solution of (1S)-1-pyridin-3-ylbutan-1-amine (600 mg, 4.0 mmol) in ethanol (20 mL) was added 2,4-dichloro-5-methylpyrimidine (717 mg, 4.4 mmol) and diisopropylethylamine (1.4 mL, 8 mmol). The solution was heated at reflux for 24 h after which time the solvent was removed under reduced pressure. The residue was dissolved in ethyl acetate (30 mL) and washed with H₂O (2×15 mL), brine (15 mL) and dried (Na₂SO₄). The residue remaining after concentration in vacuo was chromatographed using ethyl acetate-hexanes (9:1) as eluant to separate the desired product (370 mg).

¹H-n.m.r. (CDCl₃) δ 0.96 (t, 3H, J=7.2 Hz, CH₃), 1.23-1.52 (m, 2H, CH₂), 1.85-1.99 (m, 2H, CH₂), 2.03 (d, 3H, J=0.8 Hz, Ar-Me), 5.03 (br d, 1H, J=7.2 Hz, NH), 5.22-5.33 (m, 1H, CH), 7.24-7.30 (m, 1H, ArH), 7.65-7.71 (m, 1H, ArH), 7.81 (d, 1H, J=0.8 Hz, ArH), 8.51 (dd, J=5.6, 1.4 Hz, 1H, ArH), 8.64 (d, 1H, J=1.8 Hz, ArH).

Example 18

N-Ethyl-N'-[2-methoxy-4-(5-methyl-4-{[(1S)-1-pyridin-3-ylbutyl]amino}pyrimidin-2-yl)phenyl]urea

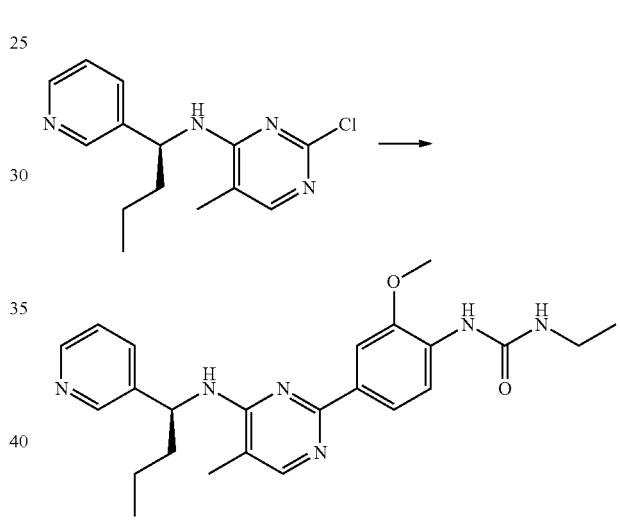

Under a nitrogen atmosphere a mixture of 2-chloro-5-methyl-N-[(1S)-1-pyridin-3-ylbutyl]pyrimidin-4-amine (277 mg, 1.0 mmol), 4-{[(ethylamino)carbonyl]amino}-3-methoxyphenylboronic acid pinacol diester (416 mg, 1.3 mmol), tetrakis(triphenylphosphine)palladium(0) (116 mg, 0.1 mmol) in toluenen-propanol (12 mL, 3:1) was treated with 2M aqueous sodium carbonate solution (750 μL, 1.5 mmol). The resulting mixture was stirred vigorously whilst being heated at 100° C. for 17 hours. Once cool ethyl acetate (25 mL) was added and the mixture washed with H₂O (6×15 mL), brine (20 mL) and dried (Na₂SO₄). Removal of solvent in vacuo then yielded crude product, which was purified by column chromatography using dichloromethane-methanol-aqueous ammonia (93:7:1) as eluent to furnish the product (110 mg, 57%).

¹H-n.m.r. (CDCl₃) δ 0.99 (t, 3H, J=7.4 Hz, CH₃), 1.18 (t, 3H, J=7.2 Hz, CH₃), 1.33-1.60 (m, 2H, CH₂), 1.82-2.02 (m, 2H, CH₂), 2.11 (s, 3H, Ar-Me), 3.25-3.39 (m, 2H, CH₂), 3.87 (s, 3H, OMe), 4.80-4.96 (m, 2H, 2×NH), 5.26-5.36 (m, 1H, CH), 6.98 (br s, 1H, Ar—NHCONH), 7.22-7.28 (m, 1H, ArH), 7.67-7.72 (m, 2H, 1H, ArH), 7.83-7.88 (m, 1H, ArH), 8.05 (d, 1H, J=0.8 Hz, ArH), 8.10 (d, 1H, J=8.2 Hz, ArH), 8.47 (dd, 1H, J=6.6, 1.8 Hz, ArH), 8.69 (d, 1H, J=2.0 Hz, ArH).

Example 19

6-Chloro-N-(1-pyridin-3-ylbutyl)pyrimidin-4-amine

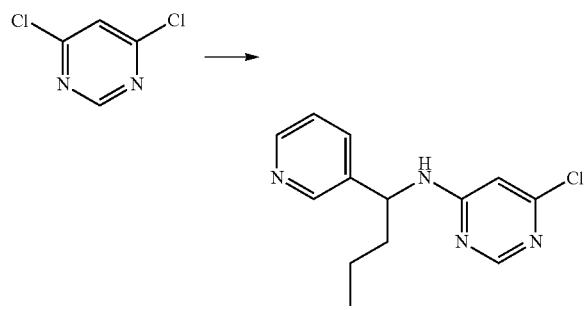

To a solution of 1-pyridin-3-ylbutan-1-amine (100 mg, 0.67 mmol) in ethanol (4 mL) was added 4,6-dichloropyrimidine (109 mg, 0.73 mmol) and diisopropylethylamine (232 µL, 1.33 mmol). The solution was stirred for 3 days after which time the solvent was removed under reduced pressure. The residue was dissolved in ethyl acetate (25 mL) and washed with $H_2O$ (3×15 mL), brine (15 mL) and dried ($Na_2SO_4$). The residue remaining after concentration in vacuo was chromatographed using ethyl acetate-hexanes (4:6-9:1) as eluant to separate the desired product (28 mg).

$^1$H-n.m.r. (CDCl$_3$) δ 0.96 (t, 3H, J=7.2 Hz, CH$_3$), 1.22-1.51 (m, 2H, CH$_2$), 1.76-1.96 (m, 2H, CH$_2$), 4.76 (br s, 1H, CH), 5.63 (br s, 1H, NH), 6.23 (s, 1H, ArH), 7.26-7.32 (m, 1H, ArH), 7.59-7.65 (m, 1H, ArH), 8.33 (s, 1H, ArH), 8.53-8.56 (m, 1H, ArH), 8.60 (d, 1H, J=1.8 Hz, ArH).

Example 20

2-Methoxy-4-{6-[(1-pyridin-3-ylbutyl)amino]pyrimidin-4-yl}phenol

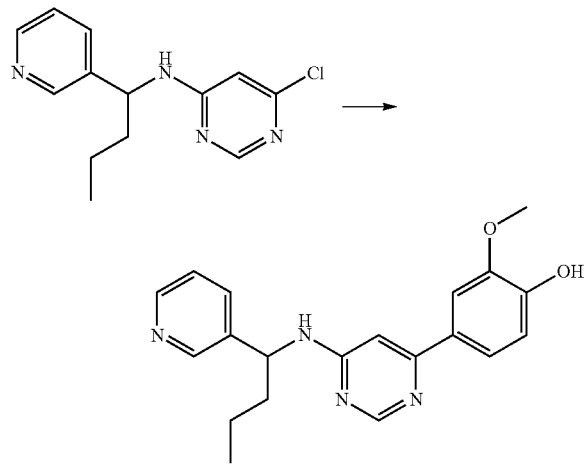

Using an analogous procedure to that described in Example 12, reaction of 6-chloro-N-(1-pyridin-3-ylbutyl)pyrimidin-4-amine (24 mg, 0.09 mmol) with 4-(4,4,5,5-tetramethyl-1,3,2-dioxaborolan-2-yl)phenol (27 mg, 0.11 mmol) afforded the desired product as a brown foam (12 mg).

$^1$H-n.m.r. (CDCl$_3$) δ 0.97 (t, 3H, J=7.2 Hz, CH$_3$), 1.32-1.55 (m, 2H, CH$_2$), 1.83-1.95 (m, 2H, CH$_2$), 3.94 (s, 3H, OMe), 4.87 (br s, 1H, CH), 5.43 (br s, 1H, NH), 6.50 (s, 1H, ArH), 6.93 (d, 1H, J=8.4 Hz, ArH), 7.25-7.31 (m, 2H, ArH), 7.55 (d, 1H, J=2.0 Hz, ArH), 7.66-7.71 (m, 1H, ArH), 8.53 (dd, 1H, J=4.9, 1.6 Hz, ArH), 8.58 (d, 1H, J=1.6 Hz, ArH), 8.66 (d, 1H, J=2.0 Hz, ArH).

Screening

Compound Dilution

For screening purposes, compounds were diluted in 96 well plates at a concentration of 20 µM. Plates were warmed at 37° C. for 30 minutes before assay.

Growth and Maintenance of Cancer Cell Lines

K562 (Chronic Myeloid Leukemia), PC3 (Prostate Cancer), and DU145 (Prostate Cancer) were obtained from the American Type Culture Collection (ATCC). K562 was grown in RPMI, with 10% FBS with Glutamx added. DU145 cells were cultured in DMED, with 10% FBS and Glutamx and MEM non-essential amino acids added. PC3 cells were grown in F12K medium, with 10% FBS and Glutamx and MEM non-essential amino acids added. All cells were grown at 37° C. in 5% $CO_2$.

Establishment of TEL:JAK Cell Lines

The coding region encompassing nucleotides 1-487 of TEL was amplified by PCR using the oligonucleotides 5TEL (5'-GGA GGA TCC TGA TCT CTC TCG CTG TGA GAC-3') (SEQ ID NO: 1) and 3TEL (5'-AGGC GTC GAC TTC TTC TTG ATG GTT CTG-3') (SEQ ID NO: 2) and U937 mRNA as template. A BamH I site was incorporated into the 5TEL primer, and a Sal I site was incorporated into the 3TEL primer. The regions encompassing the kinase domain of JAK2 (nucleotides 2994-3914; JAK2F 5'-ACGC GTC GAC GGT GCC TTT GAA GAC CGG GAT-3 (SEQ ID NO: 3); JAK2R 5'-ATA GTT TAG CGG CCG CTC AGA ATG AAG GTC ATT T-3') (SEQ ID NO: 4) and JAK3 (nucleotides 2520-3469; JAK3F 5'-GAA GTC GAC TAT GCC TGC CAA GAC CCC ACG ATC TT-3' (SEQ ID NO: 5); JAK3R 5'-GGA TCT AGA CTA TGA AAA GGA CAG GGA GTG GTG TTT-3' (SEQ ID NO: 6)) were generated by PCR using Taq DNA polymerase (Gibco/BRL) and U937 mRNA as template. A Sal I site was incorporated into the forward primer of JAK2 and JAK3, a Not I site was incorporated into the JAK2 reverse primer and a Xba I site was added to the reverse primer of JAK3.

A TEL/Jak2 fusion was generated by digestion of the TELPCR product with BamH I/Sal I, digestion of the JAK2 PCR product with Sal I/Not I followed by ligation and subcloning into the mammalian expression Vector pTRE 2 (Clontech) digested with BamH I-Not I (pTELJAK2). For JAK3 Sal I/Not I cleaved kinase domain PCR product was ligated with BamH I/Sal I cleaved TELproduct followed by ligation into BamH I/Not I cleaved pTRE2 (pTELJAK3).

The growth factor dependent myelomonocytic cell line BaF3 bearing the pTET-off plasmid (Clontech) was transfected with either pTELJAK2 or pTELJAK3 and the cells selected for factor independent growth. BaF 3 wild type cells were cultured in DMEM 10% FCS, 10% WEHI 3B conditioned medium. BaF3 TELJAK cells were cultured in DMEM 10% Tet-System Approved FBS (without WEHI 3B conditioned medium).

Cellular assays were performed as follows:

Cell suspensions were prepared by harvesting cells from culture. (Cells used in this test should be in later log phase growth and high viability.) Cells were diluted in correct growth medium to 1.1× final concentration (from 50000 cell/mL to 200,000 cell/mL, depending on cell line).

Compounds to be tested were added (10 μL, 10× final concentration) to a flat bottom 96-well plate. The cellular suspension (90 μL per well) was added, and the plate incubated for 40 hr at 37° C., 5% $CO_2$. MTT (20 μL per well, 5 mg/mL in PBS) was added and the plates were returned to the incubator for a further 6 hours. Lysis buffer (100 μL per well, 10% SDS, 0.01N HCl) was added and the plate stored in the incubator overnight. The plate was then read at 590 nm.

Tubulin Assay

Turbidometric assays of microtubule assembly were performed by incubating microtubule protein in cuvettes at 37° C. in a thermostatically controlled spectrophotometer measuring the change in absorbance at 340 nm over time. The microtubule protein was incubated with the each test compound at 0° C. and polymerisation was initiated by addition of 1 mM GTP, prior to heating to 37° C.

Results

The activity of a range of compounds is shown in Tables 1 and 2. Compounds that exhibited a capacity to inhibit greater than 50% of cellular growth at a concentration of 20 μM are designated as "+"; compounds which did not inhibit 50% of cellular growth at 20 μM are designated as "−"; compounds which were not tested are designated as "NT". Likewise, compounds which inhibited tubulin polymerisation by greater than 50% at 50 μM are designated as "+"; compounds which did not inhibit tubulin polymerisation by 50% at 50 μM are designated as "−"; and compounds which were not tested are designated as "NT".

TABLE 1

| CHEMISTRY | DU145 | PC3 | K562 | TelJak2 | TelJak3 | Tubulin |
|---|---|---|---|---|---|---|
| 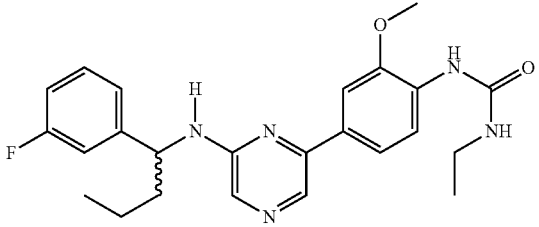 [SMILES: CCCC(Nc1cncc(-c2ccc(NC(=O)NCC)c(OC)c2)n1)c1cccc(F)c1] C24H28FN5O2 | + | + | + | + | + | + |
| 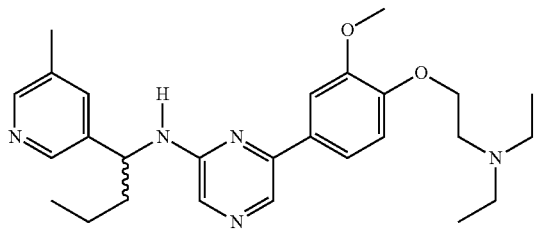 [SMILES: CCCC(Nc1cncc(-c2ccc(OCCN(CC)CC)c(OC)c2)n1)c1cncc(C)c1] C27H37N5O2 | − | − | + | + | + | NT |
| 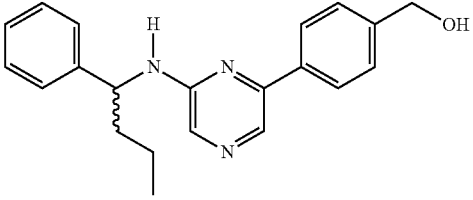 [SMILES: CCCC(Nc1cncc(-c2ccc(CO)cc2)n1)c1ccccc1] C21H23N3O | + | + | + | + | + | + |
| 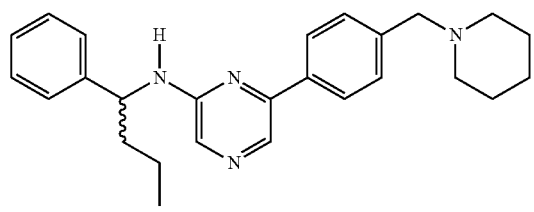 [SMILES: CCCC(Nc1cncc(-c2ccc(CN3CCCCC3)cc2)n1)c1ccccc1] C26H32N4 | − | − | − | + | + | NT |

TABLE 1-continued
| CHEMISTRY | DU145 | PC3 | K562 | TelJak2 | TelJak3 | Tubulin |
|---|---|---|---|---|---|---|
| 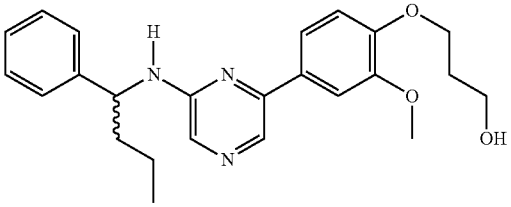 [SMILES: CCCC(Nc1cncc(-c2ccc(OCCCO)c(OC)c2)n1)c1ccccc1]<br>C24H29N3O3 | + | + | + | + | + | + |
| 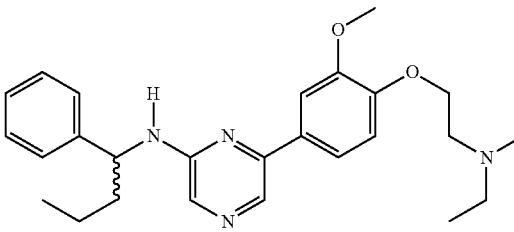<br>C27H36N4O2 | + | + | + | + | + | + |
| 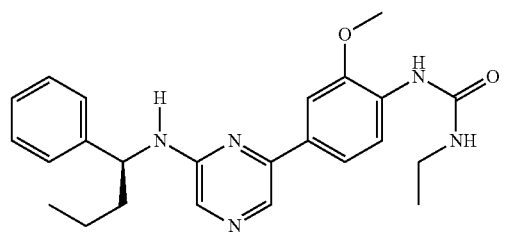 [SMILES: CCC[C@H](Nc1cncc(-c2ccc(NC(=O)NCC)c(OC)c2)n1)c1ccccc1]<br>C24H29N5O2 | + | + | + | + | + | + |
| 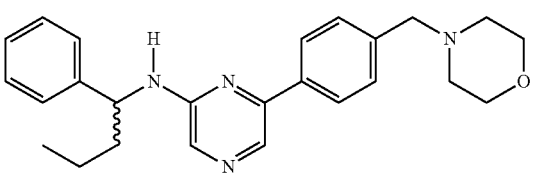 [SMILES: CCCC(Nc1cncc(-c2ccc(CN3CCOCC3)cc2)n1)c1ccccc1]<br>C25H30N4O | − | − | − | + | − | NT |
| 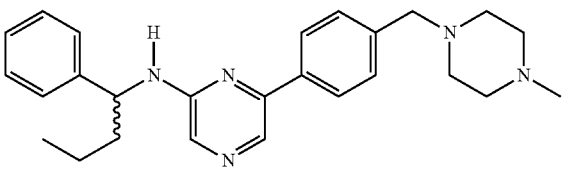 [SMILES: CCCC(Nc1cncc(-c2ccc(CN3CCN(C)CC3)cc2)n1)c1ccccc1]<br>C26H33N5 | − | − | − | + | + | NT |
| 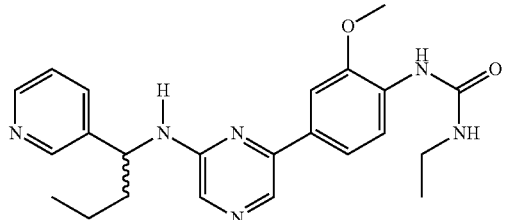<br>C23H28N6O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 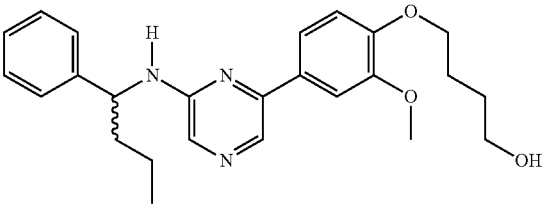 [SMILES: CCCC(Nc1cncc(-c2ccc(OCCCCO)c(OC)c2)n1)c1ccccc1]<br>C25H31N3O3 | + | + | + | + | + | + |
| 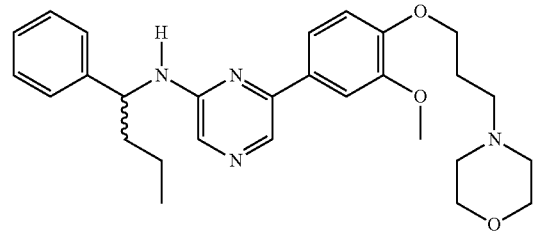 [SMILES: CCCC(Nc1cncc(-c2ccc(OCCCN3CCOCC3)c(OC)c2)n1)c1ccccc1]<br>C28H36N4O3 | − | + | + | + | + | NT |
| 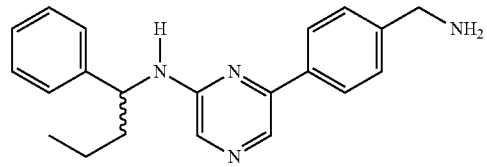 [SMILES: CCCC(Nc1cncc(-c2ccc(CN)cc2)n1)c1ccccc1]<br>C21H24N4 | + | + | + | + | + | + |
| 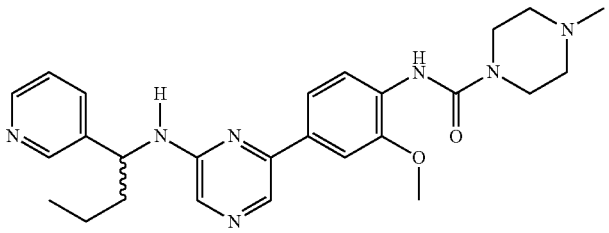 [SMILES: CCCC(Nc1cncc(-c2ccc(NC(=O)N3CCN(C)CC3)c(OC)c2)n1)c1cccnc1]<br>C26H33N7O2 | − | + | − | + | + | NT |
| 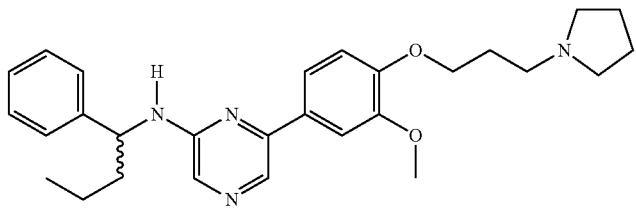 [SMILES: CCCC(Nc1cncc(-c2ccc(OCCCN3CCCC3)c(OC)c2)n1)c1ccccc1]<br>C28H36N4O2 | + | + | + | + | + | + |
| 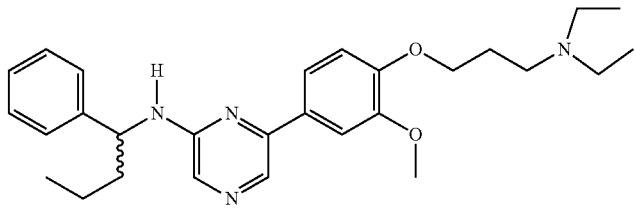 [SMILES: CCCC(Nc1cncc(-c2ccc(OCCCN(CC)CC)c(OC)c2)n1)c1ccccc1]<br>C28H38N4O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 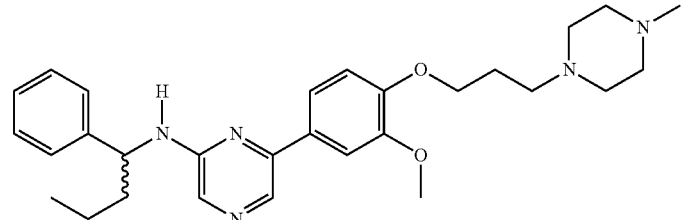<br>C29H39N5O2 | + | + | + | + | + | + |
| 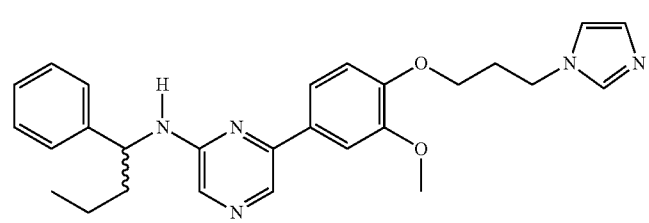 [SMILES: CCCC(Nc1cncc(-c2ccc(OCCCn3ccnc3)c(OC)c2)n1)c1ccccc1]<br>C27H31N5O2 | + | + | + | + | + | + |
| 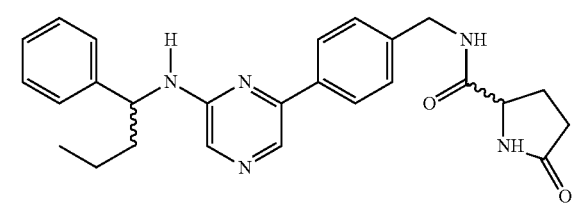 [SMILES: CCCC(Nc1cncc(-c2ccc(CNC(=O)C3CCC(=O)N3)cc2)n1)c1ccccc1]<br>C26H29N5O2 | − | − | + | + | + | NT |
| 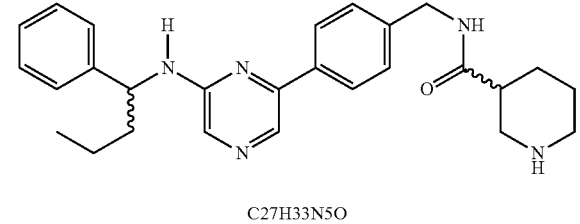<br>C27H33N5O | + | + | + | + | + | + |
| 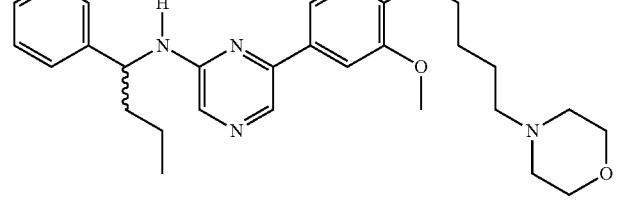<br>C29H38N4O3 | − | − | + | + | + | NT |
| 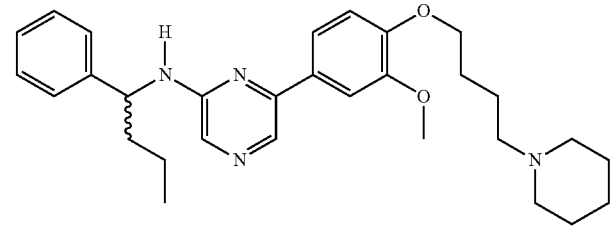 [SMILES: CCCC(Nc1cncc(-c2ccc(OCCCCN3CCCCC3)c(OC)c2)n1)c1ccccc1]<br>C30H40N4O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 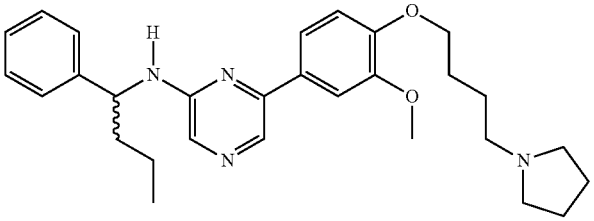 [SMILES: CCCC(Nc1cncc(-c2ccc(OCCCCN3CCCC3)c(OC)c2)n1)c1ccccc1]<br>C29H38N4O2 | + | + | + | + | + | + |
| 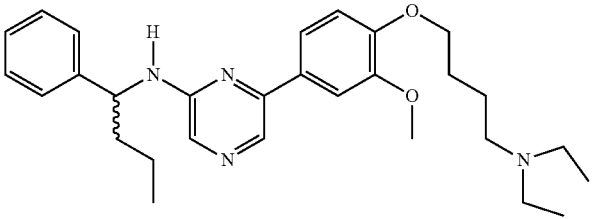 [SMILES: CCCC(Nc1cncc(-c2ccc(OCCCCN(CC)CC)c(OC)c2)n1)c1ccccc1]<br>C29H40N4O2 | + | + | + | + | + | + |
| 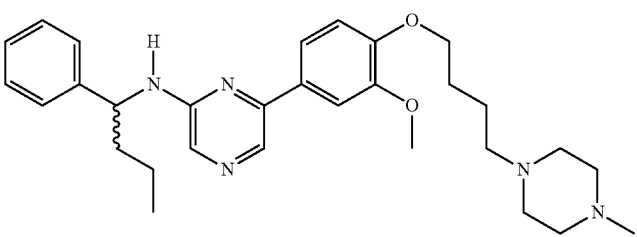 [SMILES: CCCC(Nc1cncc(-c2ccc(OCCCCN3CCN(C)CC3)c(OC)c2)n1)c1ccccc1]<br>C30H41N5O2 | + | + | + | + | + | + |
| 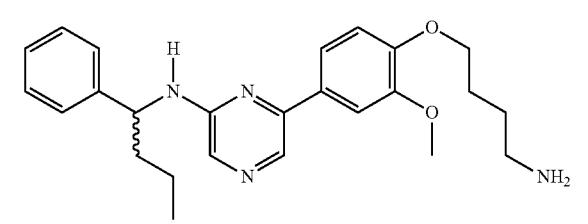 [SMILES: CCCC(Nc1cncc(-c2ccc(OCCCCN)c(OC)c2)n1)c1ccccc1]<br>C25H32N4O2 | + | + | + | + | + | + |
| 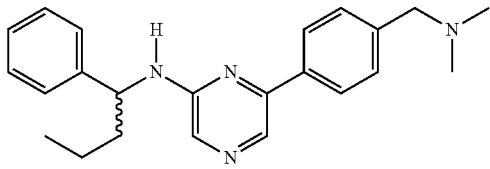 [SMILES: CCCC(Nc1cncc(-c2ccc(CN(C)C)cc2)n1)c1ccccc1]<br>Chemistry 546 | − | − | + | + | + | NT |
| 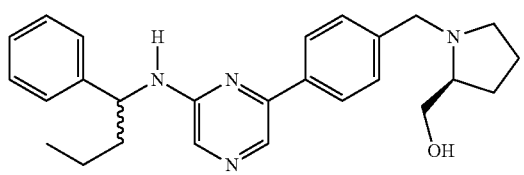 [SMILES: CCCC(Nc1cncc(-c2ccc(CN3CCC[C@H]3CO)cc2)n1)c1ccccc1]<br>C26H32N4O | − | − | + | + | + | NT |

TABLE 1-continued
| CHEMISTRY | DU145 | PC3 | K562 | TelJak2 | TelJak3 | Tubulin |
|---|---|---|---|---|---|---|
| 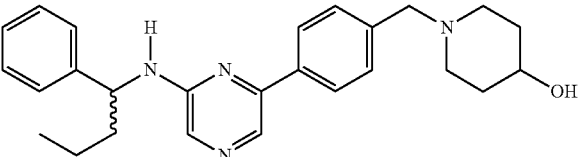<br>C26H32N4O | − | − | + | + | + | NT |
| 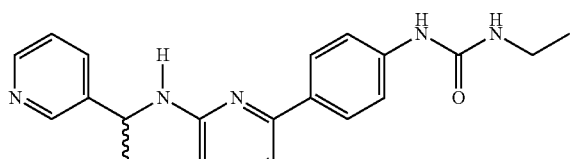<br>C22H26N6O | − | − | + | + | + | NT |
| 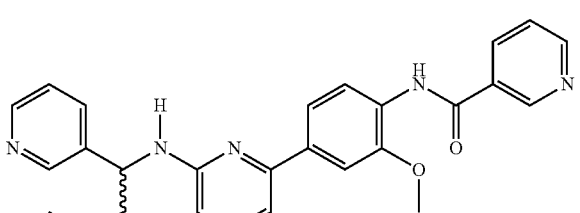<br>C26H26N6O2 | − | − | + | + | + | NT |
| 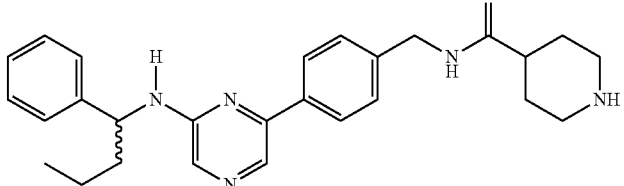<br>C27H33N5O | + | + | + | + | + | + |
| 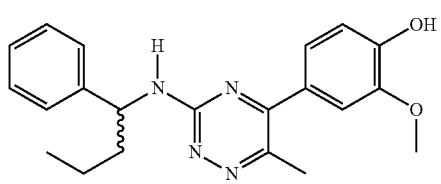 [SMILES: CCCC(Nc1nnc(C)c(-c2ccc(O)c(OC)c2)n1)c1ccccc1]<br>C21H24N4O2 | + | + | + | + | + | + |
| 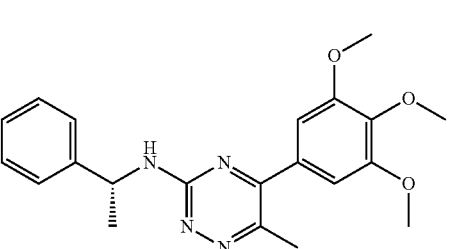<br>C21H24N4O3 | − | − | − | + | + | NT |

TABLE 1-continued
| CHEMISTRY | DU145 | PC3 | K562 | TelJak2 | TelJak3 | Tubulin |
|---|---|---|---|---|---|---|
| 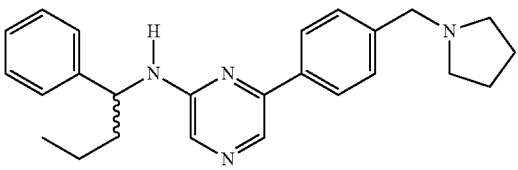 C25H30N4 | + | + | + | + | + | + |
| 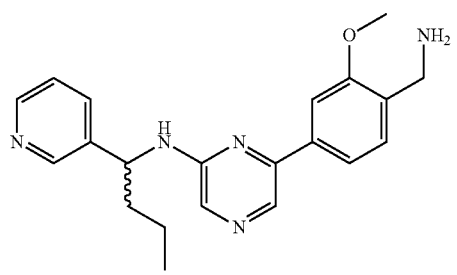 C21H25N5O | + | + | + | + | + | + |
| 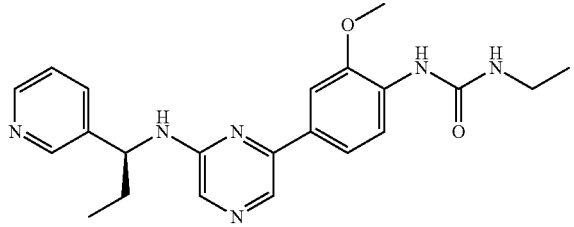 C22H26N6O2 | + | + | + | + | + | + |
| 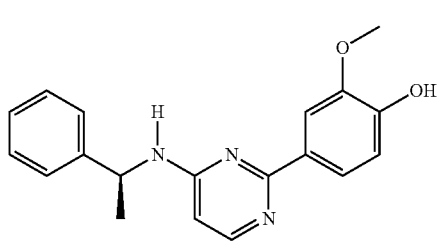 C19H19N3O2 | + | + | + | + | + | + |
| 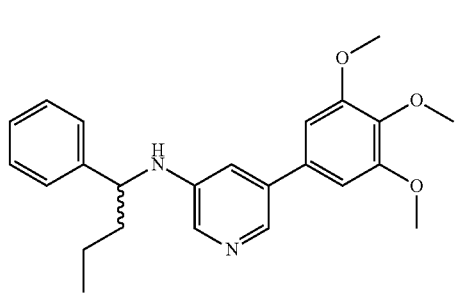 C24H28N2O3 | − | + | + | + | + | NT |

TABLE 1-continued

| CHEMISTRY | DU145 | PC3 | K562 | TelJak2 | TelJak3 | Tubulin |
|---|---|---|---|---|---|---|
| C20H20N2O2 | + | + | + | + | + | + |
| C22H24N2O2 | + | + | + | + | + | + |
| C23H26N2O | + | + | + | + | + | + |
| C26H32N6O2 | − | − | + | + | − | NT |
| C25H31N5O | − | − | − | + | + | NT |
| C28H37N5O | + | − | + | + | + | NT |

TABLE 1-continued
| CHEMISTRY | DU145 | PC3 | K562 | TelJak2 | TelJak3 | Tubulin |
|---|---|---|---|---|---|---|
| 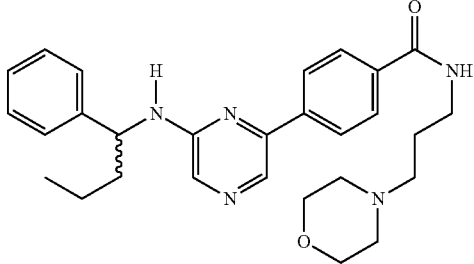 [SMILES: CCCC(Nc1cncc(-c2ccc(C(=O)NCCCN3CCOCC3)cc2)n1)c1ccccc1]<br>C28H35N5O2 | − | − | − | + | + | NT |
| 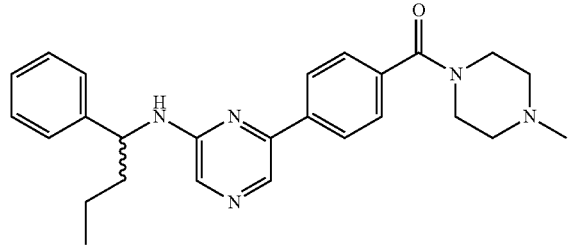 [SMILES: CCCC(Nc1cncc(-c2ccc(C(=O)N3CCN(C)CC3)cc2)n1)c1ccccc1]<br>C26H31N5O | NT | − | − | + | + | NT |
| 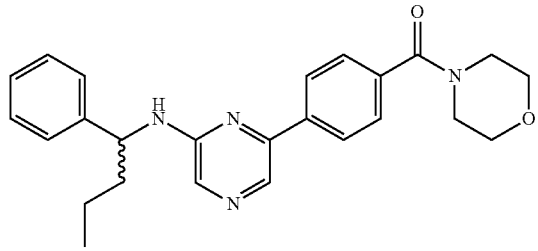 [SMILES: CCCC(Nc1cncc(-c2ccc(C(=O)N3CCOCC3)cc2)n1)c1ccccc1]<br>C25H28N4O2 | NT | − | − | + | + | NT |
| 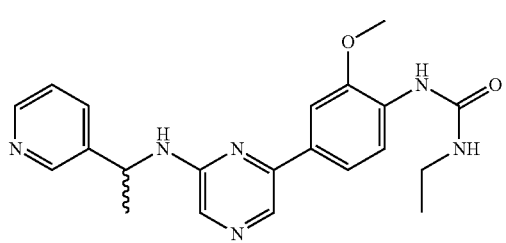 [SMILES: CCNC(=O)Nc1ccc(-c2cncc(NC(C)c3cccnc3)n2)cc1OC]<br>C21H24N6O2 | NT | − | NT | + | + | NT |
| 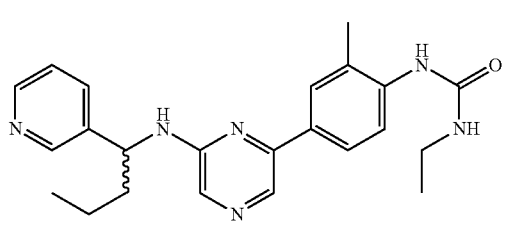 [SMILES: CCCC(Nc1cncc(-c2ccc(NC(=O)NCC)c(C)c2)n1)c1cccnc1]<br>C23H28N6O | + | + | + | + | + | + |

TABLE 1-continued
| CHEMISTRY | DU145 | PC3 | K562 | TelJak2 | TelJak3 | Tubulin |
|---|---|---|---|---|---|---|
| 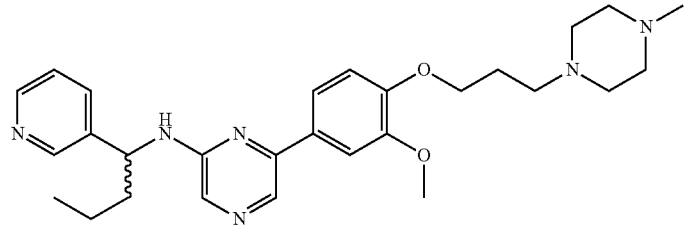 C28H38N6O2 | − | − | − | + | + | NT |
| 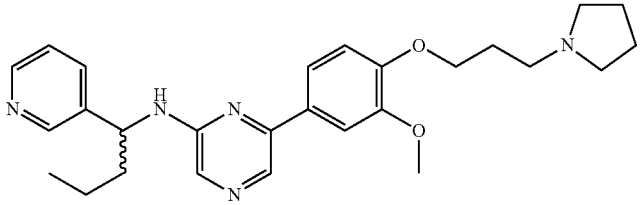 C27H35N5O2 | − | − | + | + | + | NT |
| 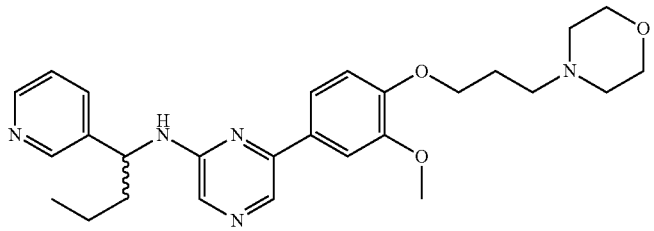 C27H35N5O3 | − | − | − | + | + | NT |
| 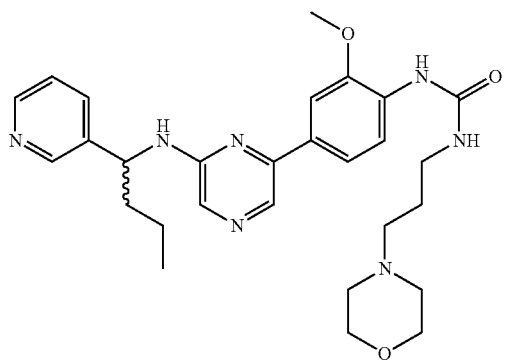 C28H37N7O3 | + | + | + | + | + | + |
| 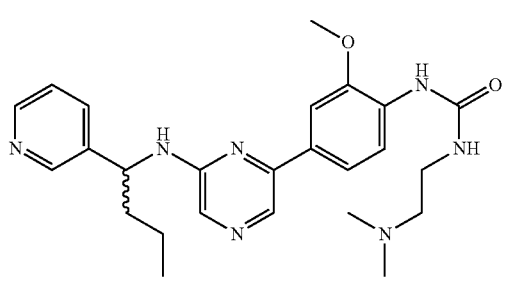 C25H33N7O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 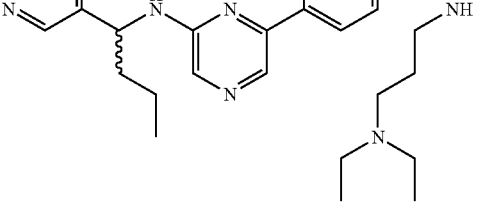<br>C28H39N7O2 | − | − | − | + | + | NT |
| 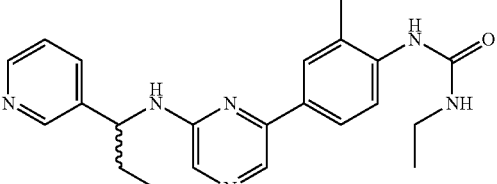<br>C24H30N6O | + | + | + | + | + | + |
| 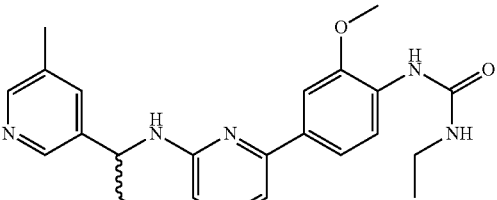<br>C24H30N6O2 | + | + | + | + | + | + |
| 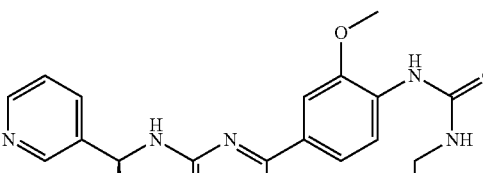<br>C23H28N6O2 | + | + | + | + | + | + |
| 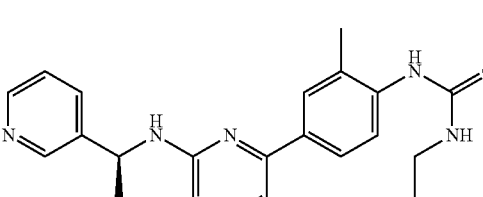<br>C23H28N6O | + | + | + | + | + | + |

TABLE 1-continued
| CHEMISTRY | DU145 | PC3 | K562 | TelJak2 | TelJak3 | Tubulin |
|---|---|---|---|---|---|---|
| 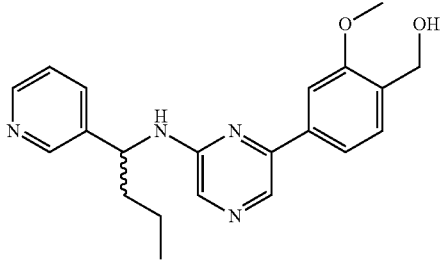 [SMILES: CCCC(Nc1cncc(-c2ccc(CO)c(OC)c2)n1)c1cccnc1]<br>C21H24N4O2 | − | − | + | + | + | NT |
| 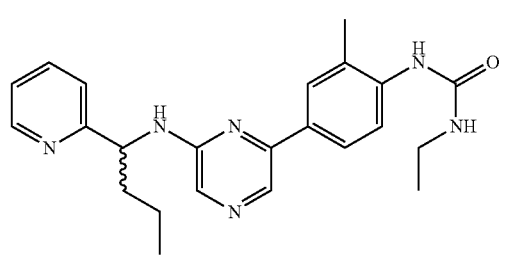 [SMILES: CCCC(Nc1cncc(-c2ccc(NC(=O)NCC)c(C)c2)n1)c1ccccn1]<br>C23H28N6O | + | + | + | + | + | + |
| 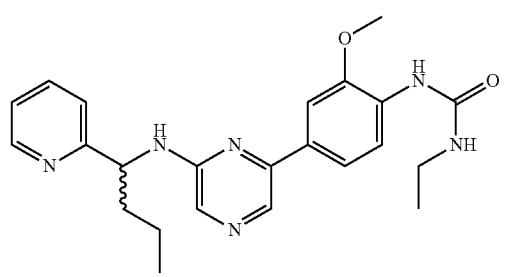 [SMILES: CCCC(Nc1cncc(-c2ccc(NC(=O)NCC)c(OC)c2)n1)c1ccccn1]<br>C23H28N6O2 | + | + | + | + | + | + |
| 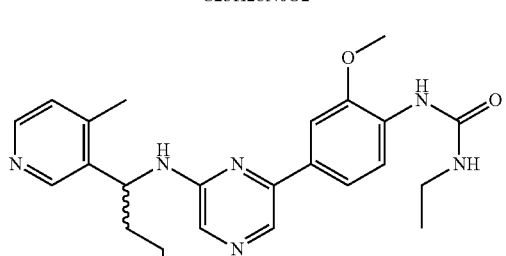<br>C24H30N6O2 | + | + | + | + | + | + |
| 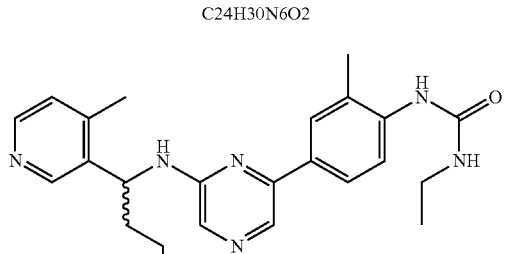<br>C24H30N6O | + | + | + | + | + | + |

TABLE 1-continued
| CHEMISTRY | DU145 | PC3 | K562 | TelJak2 | TelJak3 | Tubulin |
|---|---|---|---|---|---|---|
| 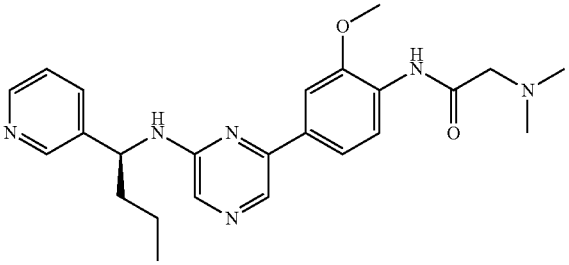 [SMILES: CCC[C@H](Nc1cncc(-c2ccc(NC(=O)CN(C)C)c(OC)c2)n1)c1cccnc1]<br>C24H30N6O2 | + | + | + | + | + | NT |
| 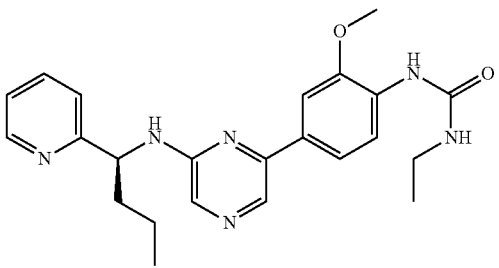 [SMILES: CCC[C@H](Nc1cncc(-c2ccc(NC(=O)NCC)c(OC)c2)n1)c1ccccn1]<br>C23H28N6O2 | + | + | + | + | + | + |
| 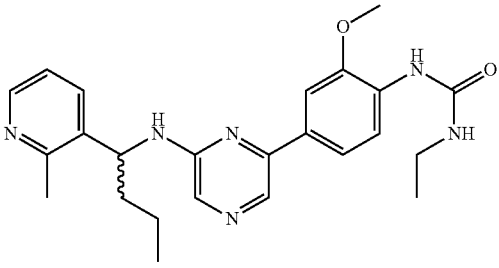 [SMILES: CCCC(Nc1cncc(-c2ccc(NC(=O)NCC)c(OC)c2)n1)c1cccnc1C]<br>C24H30N6O2 | + | + | + | + | + | + |
| 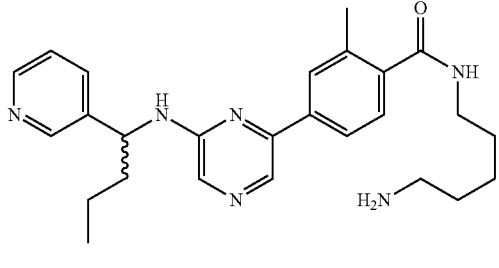 [SMILES: CCCC(Nc1cncc(-c2ccc(C(=O)NCCCCCN)c(C)c2)n1)c1cccnc1]<br>C26H34N6O | − | − | + | + | + | NT |
| 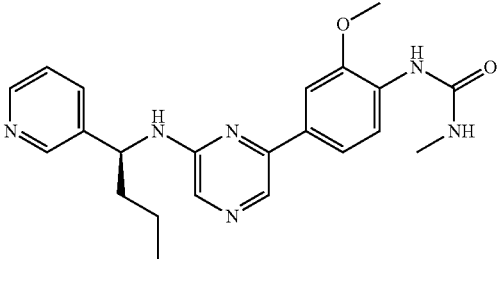 [SMILES: CCC[C@H](Nc1cncc(-c2ccc(NC(=O)NC)c(OC)c2)n1)c1cccnc1]<br>C22H26N6O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 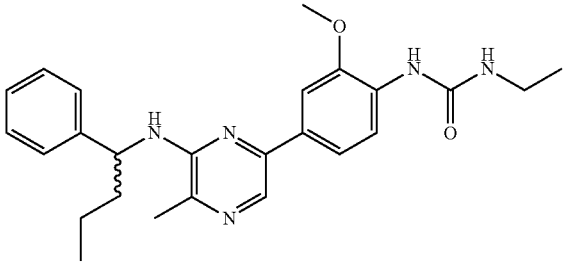 [SMILES: CCCC(Nc1nc(-c2ccc(NC(=O)NCC)c(OC)c2)cnc1C)c1ccccc1]<br>C25H31N5O2 | + | + | + | + | + | + |
| 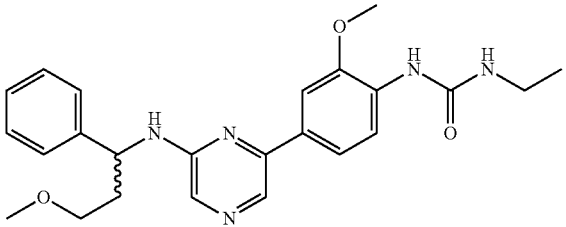 [SMILES: CCNC(=O)Nc1ccc(-c2cncc(NC(CCOC)c3ccccc3)n2)cc1OC]<br>C24H29N5O3 | + | + | + | + | + | + |
| 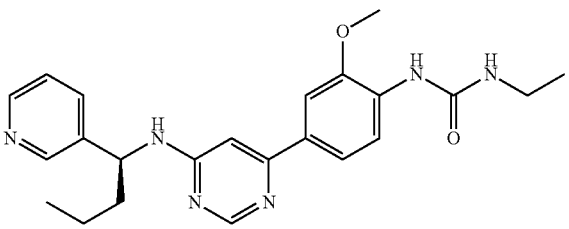 [SMILES: CCC[C@H](Nc1cc(-c2ccc(NC(=O)NCC)c(OC)c2)ncn1)c1cccnc1]<br>C23H28N6O2 | + | + | + | + | + | + |
| 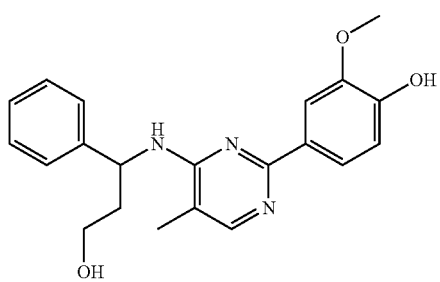 [SMILES: COc1cc(-c2ncc(C)c(NC(CCO)c3ccccc3)n2)ccc1O]<br>C21H23N3O3 | + | − | + | + | + | NT |
| 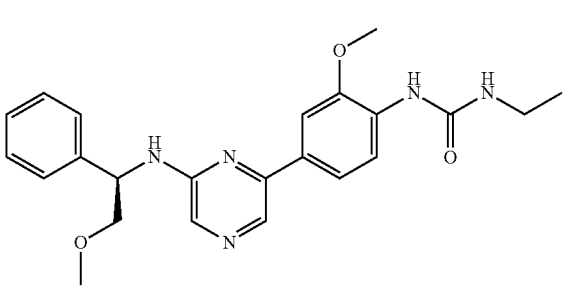 [SMILES: CCNC(=O)Nc1ccc(-c2cncc(N[C@@H](COC)c3ccccc3)n2)cc1OC]<br>C23H27N5O3 | + | + | + | + | + | + |

TABLE 1-continued
| CHEMISTRY | DU145 | PC3 | K562 | TelJak2 | TelJak3 | Tubulin |
|---|---|---|---|---|---|---|
| 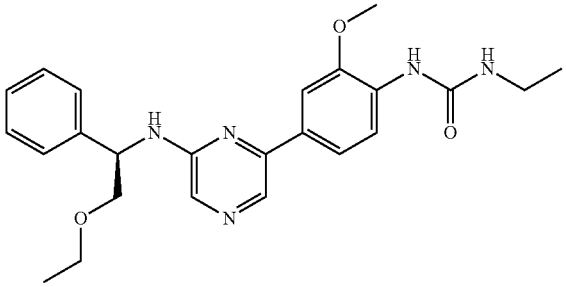 [SMILES: CCNC(=O)Nc1ccc(-c2cncc(N[C@@H](COCC)c3ccccc3)n2)cc1OC]<br>C24H29N5O3 | + | + | + | + | + | + |
| 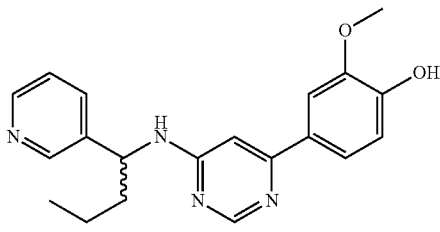 [SMILES: CCCC(Nc1cc(-c2ccc(O)c(OC)c2)ncn1)c1cccnc1]<br>C20H22N4O2 | + | + | + | + | + | + |
| 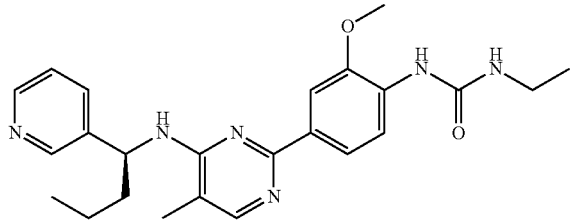 [SMILES: CCC[C@H](Nc1nc(-c2ccc(NC(=O)NCC)c(OC)c2)ncc1C)c1cccnc1]<br>C24H30N6O2 | + | + | + | + | + | + |
| 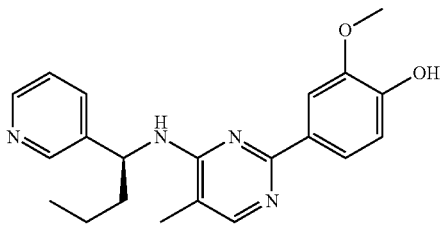 [SMILES: CCC[C@H](Nc1nc(-c2ccc(O)c(OC)c2)ncc1C)c1cccnc1]<br>C21H24N4O2 | + | + | + | + | + | + |
| 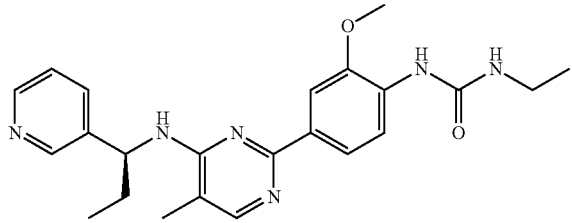 [SMILES: CCNC(=O)Nc1ccc(-c2ncc(C)c(N[C@@H](CC)c3cccnc3)n2)cc1OC]<br>C23H28N6O2 | + | + | + | + | + | + |

TABLE 1-continued
| CHEMISTRY | DU145 | PC3 | K562 | TelJak2 | TelJak3 | Tubulin |
|---|---|---|---|---|---|---|
| 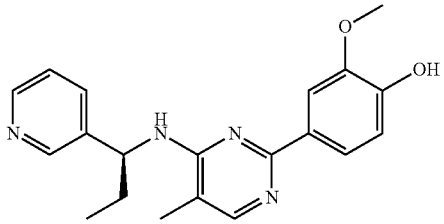 [SMILES: CC[C@H](Nc1nc(-c2ccc(O)c(OC)c2)ncc1C)c1cccnc1]<br>C20H22N4O2 | + | + | + | + | + | + |
| 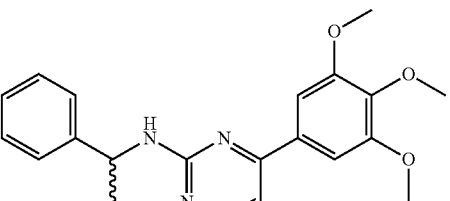<br>C23H28N4O3 | − | − | + | + | + | NT |
| 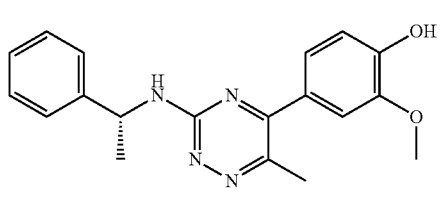 [SMILES: COc1cc(-c2nc(N[C@H](C)c3ccccc3)nnc2C)ccc1O]<br>C19H20N4O2 | − | − | + | + | + | NT |
| 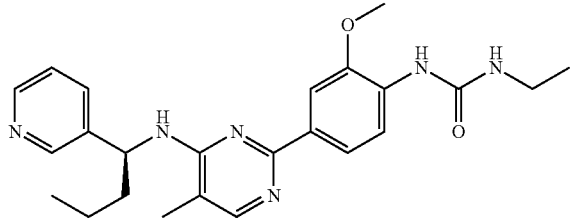 [SMILES: CCC[C@H](Nc1nc(-c2ccc(NC(=O)NCC)c(OC)c2)ncc1C)c1cccnc1]<br>C24H30N6O2 | + | + | + | + | + | + |
| 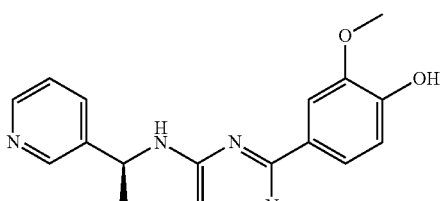<br>C21H24N4O2 | + | + | + | + | + | + |
| 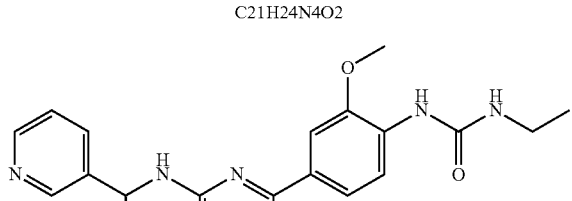<br>C23H28N6O2 | + | + | + | + | + | + |

TABLE 1-continued

| CHEMISTRY | DU145 | PC3 | K562 | TelJak2 | TelJak3 | Tubulin |
|---|---|---|---|---|---|---|
| C20H22N4O2 | + | + | + | + | + | + |
| C23H28N4O3 | − | − | + | + | + | NT |
| C19H20N4O2 | − | − | + | + | + | NT |
| C23H28N6O2 | + | + | + | + | + | + |
| C19H19N3O2 | + | + | + | + | + | + |

TABLE 2
| Chemistry | TelJak2 | TelJak3 | DU145 | Tubulin |
|---|---|---|---|---|
| 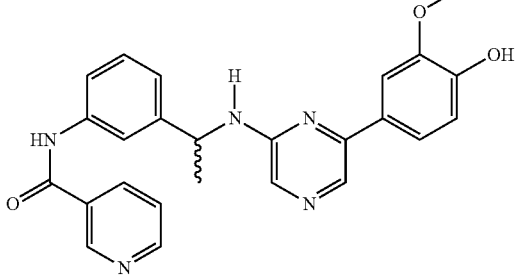 C25H23N5O3 | + | + | + | + |
| 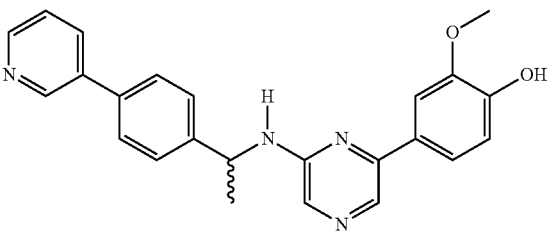 C24H22N4O2 | + | + | + | + |
| 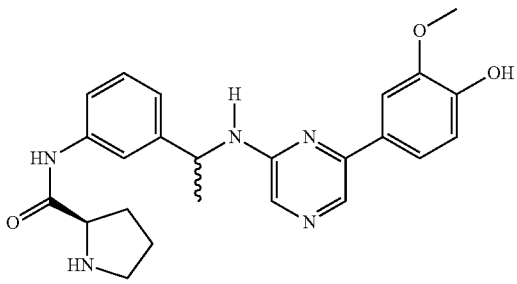 C24H27N5O3 | + | + | + | + |
| 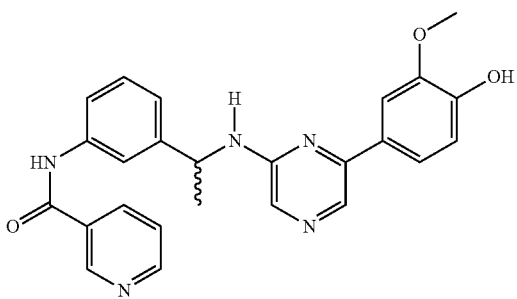 C25H23N5O3 | + | + | + | + |
| 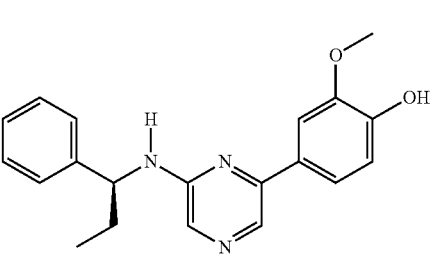 C20H21N3O2 | + | + | + | + |

TABLE 2-continued

| Chemistry | TelJak2 | TelJak3 | DU145 | Tubulin |
|---|---|---|---|---|
| 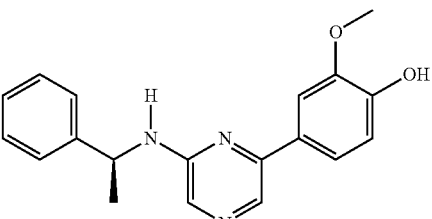<br>C19H19N3O2 | + | + | + | + |

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed anywhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Jordan M A. and Wilson L. (1998) Microtubules and actin filaments: dynamic targets for cancer chemotherapy. *Curr. Op. Cell Biol.*, 10, 123-130.
2. Jordan M A, Margolis R L, Himes R H, Wilson L., (1986) Identification of a distinct class of vinblastine binding sites on microtubules. *J. Mol. Biol.* 187:61-73
3. Rai S S, and Wolff J., (1996) Localization of the vinblastine-binding site on β-tubulin. *J. Biol. Chem.* 271:14707-11

The invention claimed is:

1. A compound selected from the group consisting of:

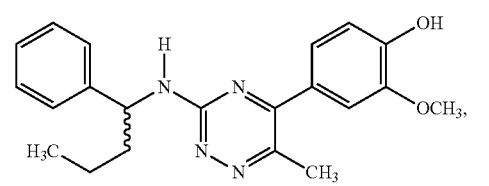

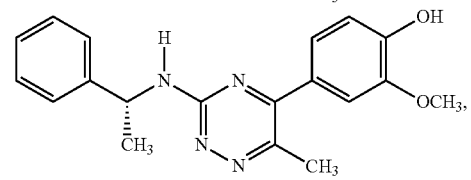

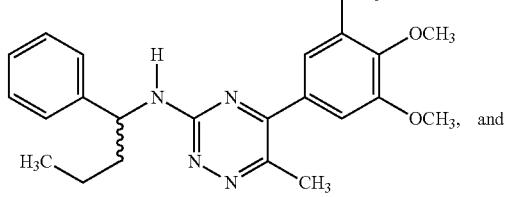

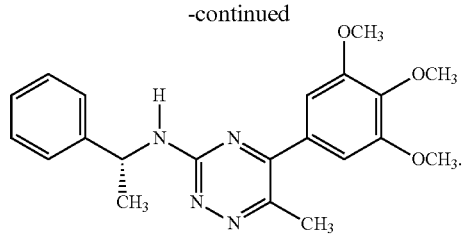

2. A composition comprising a carrier and at least one compound according to claim 1.

3. A method of modulating microtubule polymerization in a subject, said method comprising administering to the subject a therapeutically effective amount of at least one compound according to claim 1.

4. The method according to claim 3, wherein the subject suffers from a disease selected from the group consisting of cancer, vascular restenosis, atopy, cell mediated hypersensitivity, a rheumatic disease, a viral disease, an infectious disease, and an inflammatory disease.

* * * * *

```
                        SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: 5TEL primer

<400> SEQUENCE: 1
ggaggatcct gatctctctc gctgtgagac                                    30

<210> SEQ ID NO 2
<211> LENGTH: 28
<212> TYPE: DNA
<213> ORGANISM: Artificial Sequence
<220> FEATURE:
<223> OTHER INFORMATION: 3TEL primer

<400> SEQUENCE: 2
aggcgtcgac ttcttcttca tggttctg                                      28

<210> SEQ ID NO 3
<211> LENGTH: 31
<212> TYPE: DNA
<213> ORGANISM: Artificial Sequence
<220> FEATURE:
<223> OTHER INFORMATION: JAK2F primer

<400> SEQUENCE: 3
acgcgtcgac ggtgcctttg aagaccggga t                                  31
```

```
<210> SEQ ID NO 4
<211> LENGTH: 34
<212> TYPE: DNA
<213> ORGANISM: Artificial Sequence
<220> FEATURE:
<223> OTHER INFORMATION: JAK2R primer

<400> SEQUENCE: 4
atagtttagc ggccgctcag aatgaaggtc attt                              34

<210> SEQ ID NO 5
<211> LENGTH: 35
<212> TYPE: DNA
<213> ORGANISM: Artificial Sequence
<220> FEATURE:
<223> OTHER INFORMATION: JAK3F primer

<400> SEQUENCE: 5
gaagtcgact atgcctgcca agacccacg atctt                              35

<210> SEQ ID NO 6
<211> LENGTH: 36
<212> TYPE: DNA
<213> ORGANISM: Artificial Sequence
<220> FEATURE:
<223> OTHER INFORMATION: JAK3R primer

<400> SEQUENCE: 6
ggatctagac tatgaaaagg acagggagtg gtgttt                            36
```